United States Patent [19]

Yoshimura et al.

[11] Patent Number: 5,788,655
[45] Date of Patent: Aug. 4, 1998

[54] EXERCISE AMOUNT MEASURING DEVICE CAPABLE OF DISPLAYING THE AMOUNT OF EXERCISE TO BE PERFORMED FURTHER

[75] Inventors: Manabu Yoshimura, Kyoto; Maki Hasegawa; Tsukasa Hatakenaka, both of Osaka; Makoto Tabata, Kyoto; Tsutomu Yamasawa, Osaka; Masaaki Takenaka, Kyoto; Tomoo Watanabe, Kyoto; Kazuyuki Morita, Osaka, all of Japan

[73] Assignee: Omron Corporation, Kyoto, Japan

[21] Appl. No.: 528,634

[22] Filed: Sep. 7, 1995

[30] Foreign Application Priority Data

| Sep. 7, 1994 | [JP] | Japan | 6-213362 |
| Sep. 7, 1994 | [JP] | Japan | 6-213363 |
| Sep. 12, 1994 | [JP] | Japan | 6-217109 |
| Mar. 10, 1995 | [JP] | Japan | 7-050852 |

[51] Int. Cl.$^6$ .................................................. A61B 5/103
[52] U.S. Cl. .................................................. 600/587
[58] Field of Search .................................. 128/782, 774, 128/779

[56] References Cited

U.S. PATENT DOCUMENTS

| 3,797,010 | 3/1974 | Adler et al. | 128/782 |
| 4,828,257 | 5/1989 | Dyer et al. | 272/129 |
| 5,479,939 | 1/1996 | Ogino | 128/782 |

FOREIGN PATENT DOCUMENTS 5-36166  9/1993  Japan .

*Primary Examiner*—Max Hindenburg
*Assistant Examiner*—Pamela L. Wingood
*Attorney, Agent, or Firm*—Morrison & Foerster LLP

[57] ABSTRACT

Total consumed calories are indicated in an upper portion of a display. A life activity intensity of each of the past seven days and an average life activity intensity over the same period are indicated by a bar graph in a lower portion of the display. The life activity intensity is classified into rank I (light), rank II (medium), and rank III (a little heavy). A total exercise amount (i.e., total consumed calories) and a life activity intensity are calculated and automatically displayed at the end of a day.

10 Claims, 32 Drawing Sheets

FIG. 2

| AGE | MALE | FEMALE |
|---|---|---|
| 6 | 52.9 | 49.5 |
| 7 | 51.1 | 47.6 |
| 8 | 49.3 | 46.2 |
| 9 | 47.5 | 44.8 |
| 10 | 46.2 | 44.1 |
| 11 | 45.3 | 43.1 |
| 12 | 44.5 | 42.2 |
| 13 | 43.5 | 41.2 |
| 14 | 42.6 | 39.8 |
| 15 | 41.7 | 38.1 |
| 16 | 41.0 | 36.9 |
| 17 | 40.3 | 36.0 |
| 18 | 39.6 | 35.6 |
| 19 | 38.8 | 35.1 |
| 20 ~ 29 | 37.5 | 34.3 |
| 30 ~ 39 | 36.5 | 33.2 |
| 40 ~ 49 | 35.6 | 32.5 |
| 50 ~ 59 | 34.8 | 32.0 |
| 60 ~ 64 | 34.0 | 31.6 |
| 65 ~ 69 | 33.3 | 31.4 |
| 70 ~ 74 | 32.6 | 31.1 |
| 75 ~ 79 | 31.9 | 30.9 |
| 80 ~ | 30.7 | 30.0 |

FIG. 4

| LIFE ACTIVITY INDEX | LIFE ACTIVITY INTENSITY |
|---|---|
| ≤ 0.42 | I |
| 0.43 ~ 0.62 | II |
| 0.63 ~ 0.87 | III |
| ≥ 0.88 | IV |

EXERCISE AMOUNT MEASURING DEVICE CAPABLE OF DISPLAYING THE AMOUNT OF EXERCISE TO BE PERFORMED FURTHER

BACKGROUND OF THE INVENTION

1. Field of the Invention

The present invention relates to an exercise amount measuring device for measuring an exercise amount (energy expenditure) of a living body (human body) by using an acceleration sensor or the like and displaying the measured exercise amount.

2. Description of the Related Art

Conventionally, the above type of exercise amount measuring device generally consists of an acceleration sensor for detecting the body movement of a human body, an exercise amount calculation means for calculating an exercise amount of the human body based on a signal produced by the acceleration sensor, and a display section for displaying the calculated exercise amount. FIG. 33 shows an example of a display form of the display section of such an exercise amount measuring device (Japanese Examined Utility Model Publication No. Hei. 5-36166). The display section has a function of displaying a weight and a stride of a subject person, a function of displaying a calculated exercise amount or total consumed calories, and other functions.

However, the conventional exercise amount measuring device measures only the amount of exercise taken (i.e., consumed calories) and simply displays, on the display section, a numerical value of the exercise amount or the total consumed calories. Therefore, it is difficult for a subject person to judge whether his exercise was appropriate. In addition, he is not informed of the amount of exercise to take further.

Further, in the above conventional exercise amount measuring device, only the consumed calories of an exercise are calculated and displayed and the calculation method is changed only based on whether the walking (or running) pace is higher than a certain value. Therefore, a user is not informed of total consumed calories of one day, nor are consumed calories calculated and displayed when he performs an exercise in a standing or sitting state.

Further, since the above conventional exercise amount measuring device simply measures and displays consumed calories of an exercise, a user is not informed of the amount of exercise (consumption calories) necessary to consume calories of ingested food, nor can he recognize a degree and length of exercise he should perform for that purpose.

SUMMARY OF THE INVENTION

In view of the problems in the art, an object of the present invention is to provide an exercise amount measuring device which not only enables a subject person to judge more easily of the appropriateness of an exercise taken, but also allows him to know a necessary exercise amount.

Another object of the invention is to provide an exercise amount measuring device which allows a user to recognize not only total consumed calories in a prescribed period but also consumed calories of each of action types including sitting and standing, not to mention walking and running.

A further object of the invention is to provide an exercise amount measuring device which allows a user to recognize not only an exercise amount necessary to consume calories of ingested food but also a degree and a time length of exercise he should perform for the same purpose.

According to a first aspect of the invention, in an exercise amount measuring device comprising an acceleration sensor for detecting a body movement of a living body, means for calculating an exercise amount based on a detection signal of the acceleration sensor, and a display section for displaying the calculated exercise amount, a remaining target calorie value or a target exercise amount is calculated and displayed. Therefore, a user can recognize the amount of exercise to perform further.

According to another embodiment, a life activity index is calculated and displayed, for instance, so as to be classified as one of ranks that are associated with respective preset life activity intensities. Therefore, a user can recognize whether his exercise is at an appropriate level.

A difference or ratio between a target value and a measured value may be displayed. Further, an exercise time corresponding to the difference between the target value and the measured value may be displayed, which allows a user to recognize, more easily, the amount of exercise to perform further.

According to a further embodiment, an exercise amount, and a difference between a target value and a measured value or the tendency of a temporal variation of a life activity index. Therefore, a user can easily recognize a variation of exercise levels.

According to a second aspect of the invention, in an exercise amount measuring device comprising an acceleration sensor for detecting a body movement of a living body, means for calculating an exercise amount based on a detection signal of the acceleration sensor, and a display section for displaying the calculated exercise amount, a total consumed calorie (energy) value in a prescribed period (for instance, one day) is calculated and displayed. More specifically, the action of the living body is classified into a plurality of action types, and consumed calorie values of the respective action types are calculated. A total consumed calorie value is determined from the consumed calorie values thus calculated. Therefore, a user can recognize consumed calorie values of the respective action types.

According to another embodiment, the action of the living body is classified into action types including sleeping, sitting, standing, walking and running. Since they are basic actions of human life except special ones such as swimming and jumping, a total consumed calorie value of one day can be calculated correctly.

If a ratio among time lengths of the respective action types is displayed, or a pattern of occurrence of the action types is displayed in a time order at predetermined time intervals, a user can recognize his one-day life activities more precisely and can thereby improve his life attitude.

According to a third aspect of the invention, in an exercise amount measuring device comprising an acceleration sensor for detecting a body movement of a living body, means for calculating an exercise amount based on a detection signal of the acceleration sensor, and a display section for displaying the calculated exercise amount, a consumed calorie value in a prescribed period (for instance, one day) is calculated and displayed. According to another embodiment, advice is determined based on a result of comparison between ingested calorie value and a consumed calorie value, and then displayed. Therefore, a user can recognize not only an exercise amount necessary to consume calories of ingested foods, but also a balance between the ingested calorie value and the consumed calorie value.

In particular, when the ingested calorie value is larger than the consumed calorie value, a type and a time length of exercise corresponding to the calorie difference may be displayed. Conversely, when the consumed calorie value is larger than the ingested calorie value, a food and its amount corresponding to the calorie difference may be displayed. A user is allowed to recognize such information at a glance.

According to another embodiment, a tendency of whether a user is gaining or losing weight is determined and displayed. Thus, he can recognize whether which of the ingested calorie value or the consumed calorie value is larger, and therefore can manage the balance between those calorie values.

According to another embodiment, when an ingested calorie value is input, the ingested calorie value as input and an already-input ingested calorie value are displayed at the same time. Therefore, a user can easily recognize calories ingested so far (total ingested calorie value) and a ratio of the input ingested calorie value of this time to the total ingested calorie value, and is thereby allowed to manage the food ingestion easily. Further, ingested calory values can be input more easily by allowing the user to use a number that indicates a calorie value of a food, where names of foods and their calorie values are listed on a menu sheet together with numbers for the respective foods.

BRIEF DESCRIPTION OF THE DRAWINGS

FIG. 2 shows standard values of basal metabolism per body surface area of 1 m² in relation to the age and gender;

FIG. 4 shows classification of the life activity index and the life activity intensity;

DESCRIPTION OF THE PREFERRED EMBODIMENTS

Exercise amount measuring devices according to several embodiments of the present invention will be hereinafter described with reference the accompanying drawings.

Embodiment 1

Figure 1:
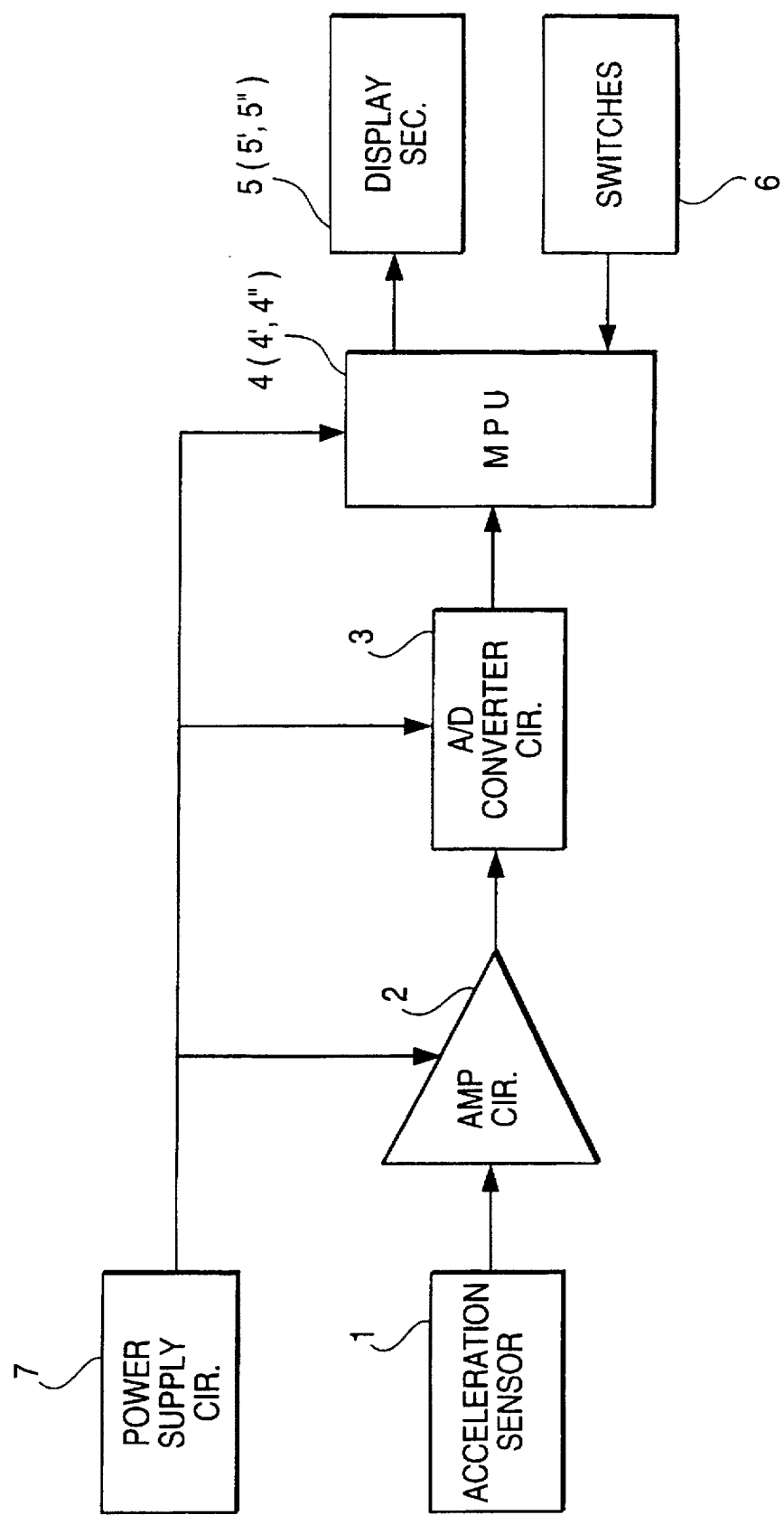
FIG. 1 is a block diagram showing the entire configuration of exercise amount measuring devices according to embodiments of the present invention.

FIG. 1 is a block diagram showing the entire configuration of an exercise amount measuring device according to a first embodiment of the invention. This exercise amount measuring device is basically the same as the conventional one except the various calculating functions and the display form, and has the following components. An acceleration sensor 1, which is mounted on a human body, detects its body movement. An amplifier circuit 2 amplifies a detection signal of the acceleration sensor 1. An A/D converter circuit 3 converts the amplified signal to a digital signal. A MPU 4 has a function of calculating an exercise amount based on the received digital signal, a function of calculating remaining target calories using estimated consumption calories of a prescribed period (for instance, one day), a function of calculating a target exercise amount that a human body is desired to perform in the prescribed period (one day), a function of calculating a life activity index, and other functions. A display (display section) 5 displays a gender, age, exercise amount, life activity intensity, etc. Switches 6 include a power on/off switch, a select switch for selecting the kind of display, and a switch for inputting a gender, an age, etc. Further, the exercise amount measuring device has a power supply circuit 7.

To allow the various calculating functions to calculate the exercise amount, life activity intensity, etc., the exercise amount measuring device needs information of a basal metabolism. Among various methods of determining the basal metabolism is a method according to Equation (1).

$$B = B_s \times S \tag{1}$$

where $B_s$: standard value of basal metabolism per body surface area of 1 m² (kcal/m²/hour)

S: body surface area (m²) = {weight (kg)}$^{0.444}$ × {height (cm)}$^{0.663}$ × 0.008883.

Figure 3:
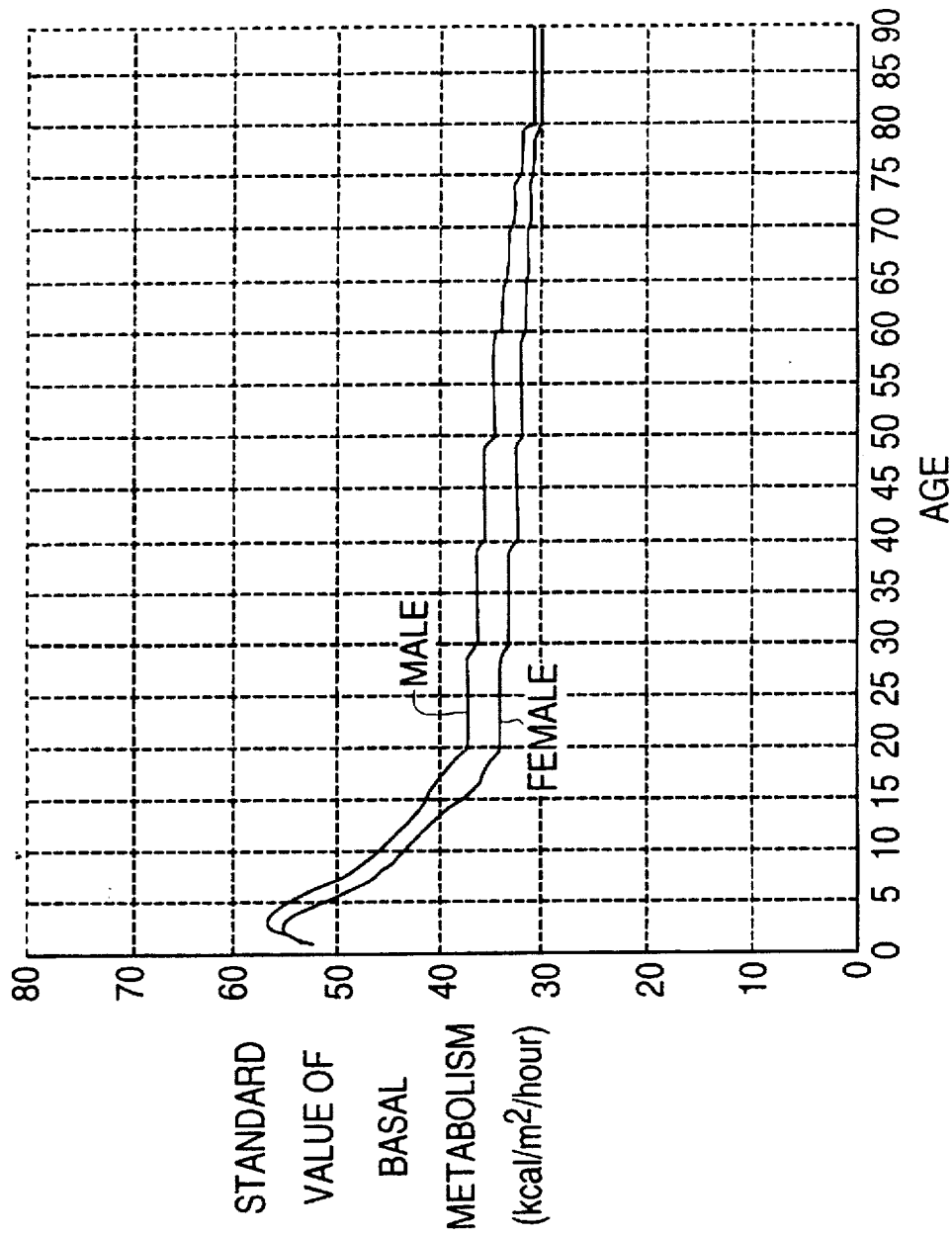
FIG. 3 is a graphical representation of FIG. 2.

It is noted that Equation (1) is applicable only to persons of age 6 or older. Further, $B_s$ depends on the gender and age, and can be determined from Table II-1 of "The Nutrition Amount Necessary for Japanese (5th revised edition)." (Refer to FIG. 2 (table showing standard values of basal metabolism in relation to the gender and age) and FIG. 3 (graph showing a relationship between the age and the standard value of basal metabolism).)

On the other hand, the life activity index is calculated in the following manner. The total energy metabolism per day (A) is expressed as $$A = B \cdot \chi + B + 0.1 \qquad (2)$$

where $B \cdot \chi$ is the energy consumed by an exercise etc. ($\chi$: life activity index), B is the basal metabolism, and 0.1·A is the amount of metabolism due to the specific dynamic action (i.e., the energy necessary for decomposing and absorbing food ingested). Modifying Equation (2), $$\chi = 0.9(A/B) - 1 \qquad (3)$$

The actually measured exercise amount and the calculated basal metabolism may be used as the total energy metabolism A and the basal metabolism B, respectively.

By classifying the calculated life activity index $\chi$ into, for instance, four ranks shown in FIG. 4 so that they are associated with respective life activity intensities, it becomes possible to inform a subject person of the level of exercise. In the classification of FIG. 4, life activity intensity I is lightest and life activity intensity IV is heaviest. Apparently the classification may be made into the number of ranks other than four; that is, it may be made into three or five ranks.

The target exercise amount is calculated aiming at the above life activity index $\chi$. Modifying Equation (2), the target exercise amount A is expressed as $$A = (10/9)(1+\chi)B.$$

Substituting $\chi = 0.5$ ($\chi$ is set at 0.5 that is an appropriate value), $$A = 1.67 \times B \qquad (4)$$

Next, a description will be made of the display form on the display screen of the display 5. In an example of FIG. 5, the display screen is divided into an upper portion 10 and a lower portion 11. An exercise amount (i.e., total consumed calories (kcal)) is indicated in the upper portion as a numerical value, and life activity intensities of a past week and an average life activity intensity over the same week are indicated in the lower portion 11 as a bar graph. The life activity intensity is classified into three ranks: I (light), II (medium), and III (a little heavy), where the target level is set at rank II. With this display form, a life activity amount (total consumed calories) and an activity intensity are calculated and automatically displayed at the end of each day. Further, there can be displayed consumed calories and an activity intensity of each of the seven days of a past week and average consumed calories and an average activity intensity of the same seven days. To store consumed calories and activity intensities of a week, an automatic memory function may be employed, for instance. The display form of FIG. 5 allows a user to recognize, at a glance, the tendency of exercise taken in a past week.

Figure 5:
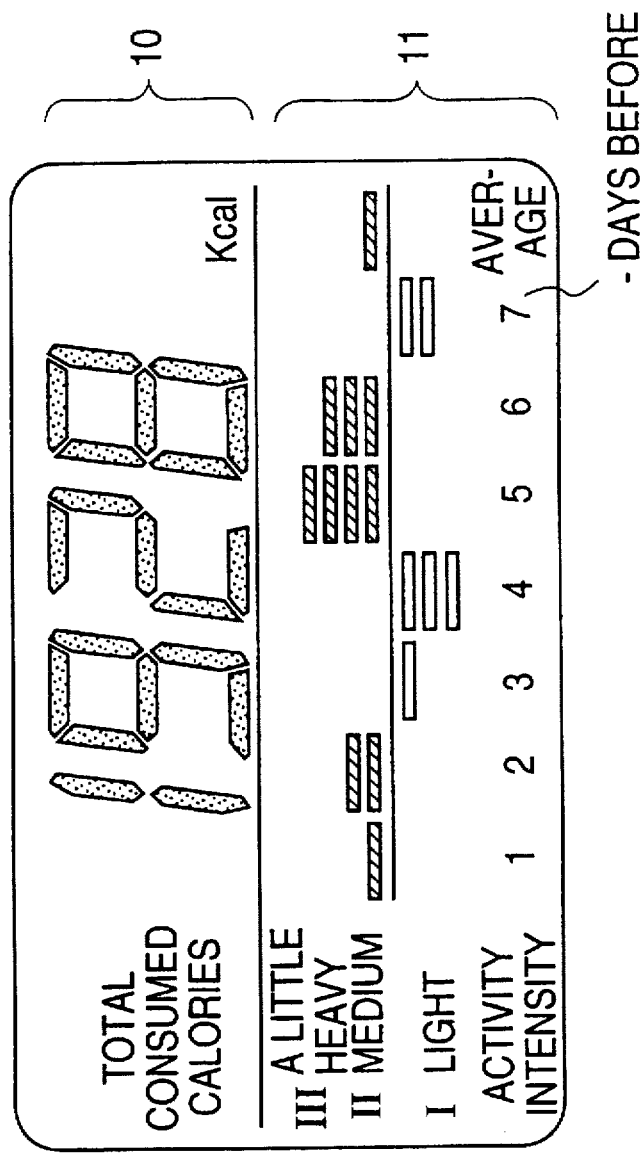
FIG. 5 shows an example of a display form of the exercise amount measuring device according to the first embodiment of the invention.
Figure 6A:
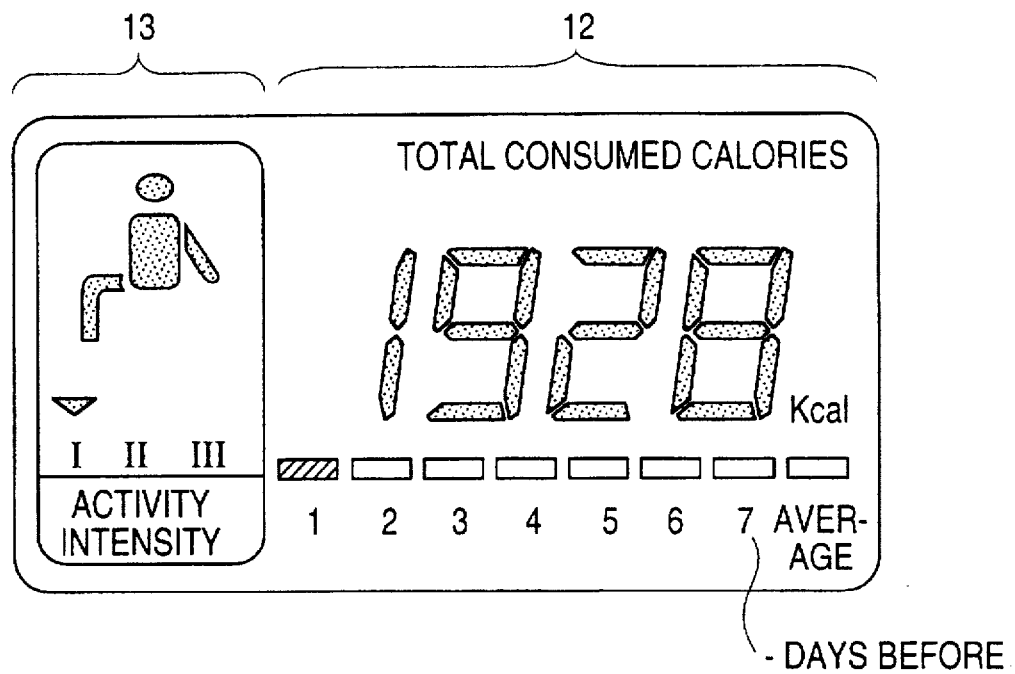
FIGS. 6A and 6B show a modified version of the display form of FIG. 5.
Figure 6B:
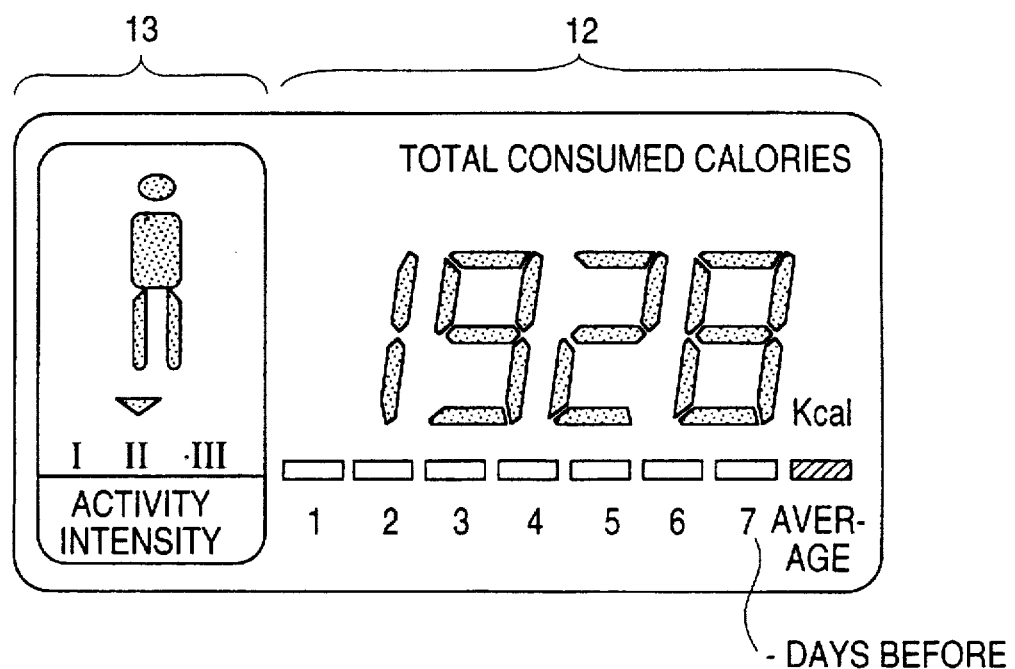

FIGS. 6A and 6B show a modified version of the display form of FIG. 5. In this display form, as in the case of FIG. 5, the total consumed calories and the three-rank activity intensity are indicated. As a specific feature of this display form, total consumed calories are indicated in a right-hand portion 12 and an activity intensity is indicated in a left-hand portion 13 with different pictures for the respective ranks of activity intensity. For example, the picture of FIG. 6A indicates a life activity amount of the preceding day, which is rank I (light). The picture of FIG. 6B indicates an average of total consumed calories of seven days, which is rank II (medium). Stored values of consumed calories and activity intensities of past seven days can be called for each day by operating the switches 6.

Figure 7:
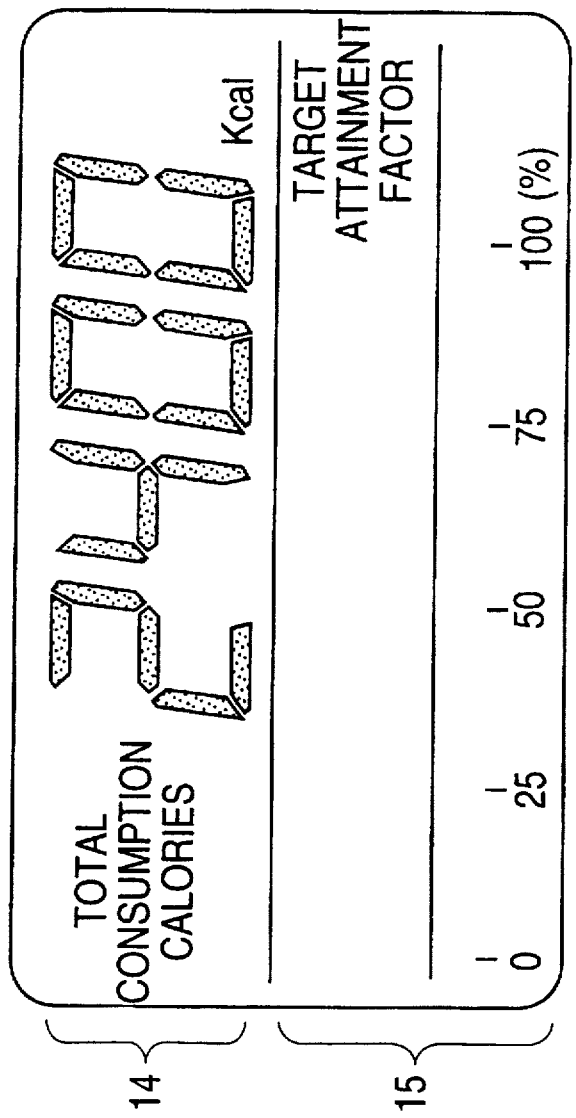
FIG. 7 and FIGS. 8A and 8B show another example of a display form in the first embodiment.
Figure 8A:
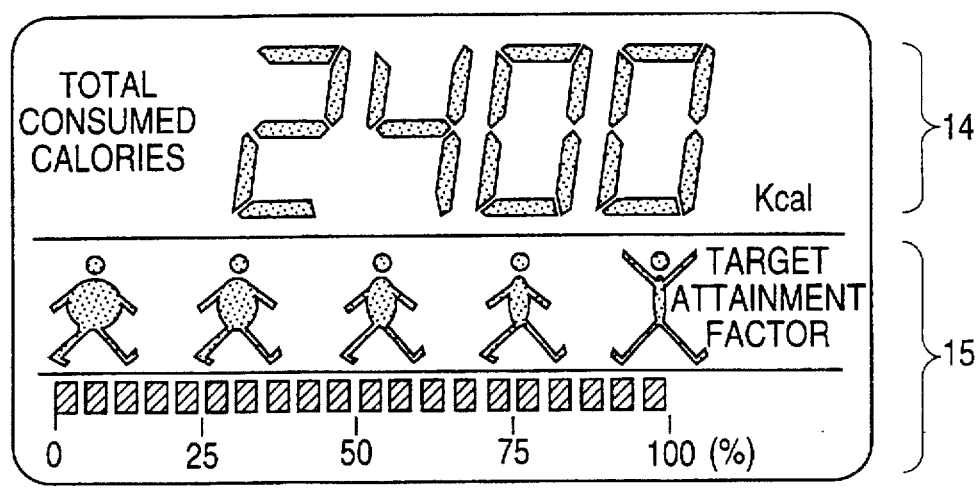
Figure 8B:
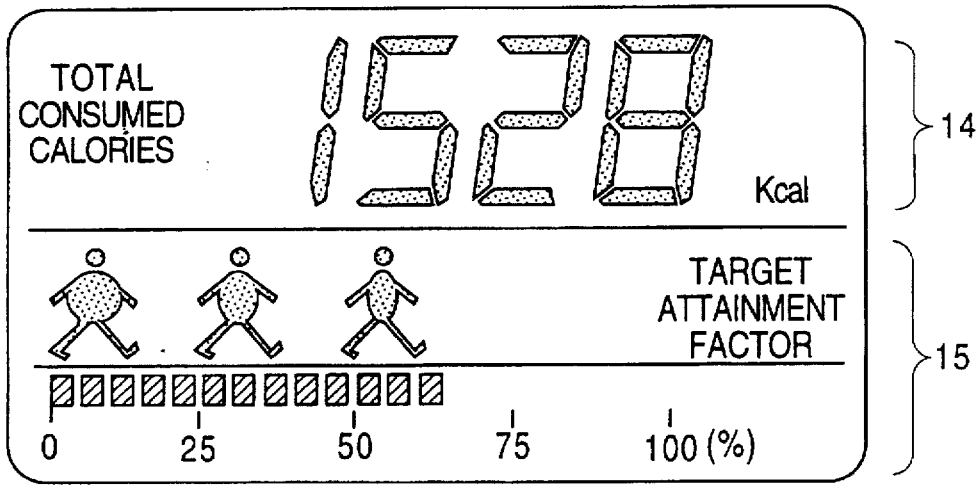

FIG. 7 shows another display form. According to this display form, once a gender, age, height and weight are input, target consumption calories suitable for that person is automatically set and displayed and an attainment factor of the target consumption calories is indicated by a bar graph and a picture. Referring to FIG. 7, target consumption calories and total consumed calories are indicated in an upper portion 14 of the display screen and a target attainment factor is indicated in a lower portion 15. For example, where the target consumption calorie value is 2,400 kcal as shown in FIG. 7 and the actually consumed calorie value is also 2,400 kcal as shown in FIG. 8A, the attainment factor is 100% and a bar graph and a picture appear as shown in FIG. 8A. On the other hand, where the actually consumed calorie value is 1,528 kcal as shown in FIG. 8B, the target attainment factor is about 65% and a bar graph and a picture appear accordingly.

Figure 9A:
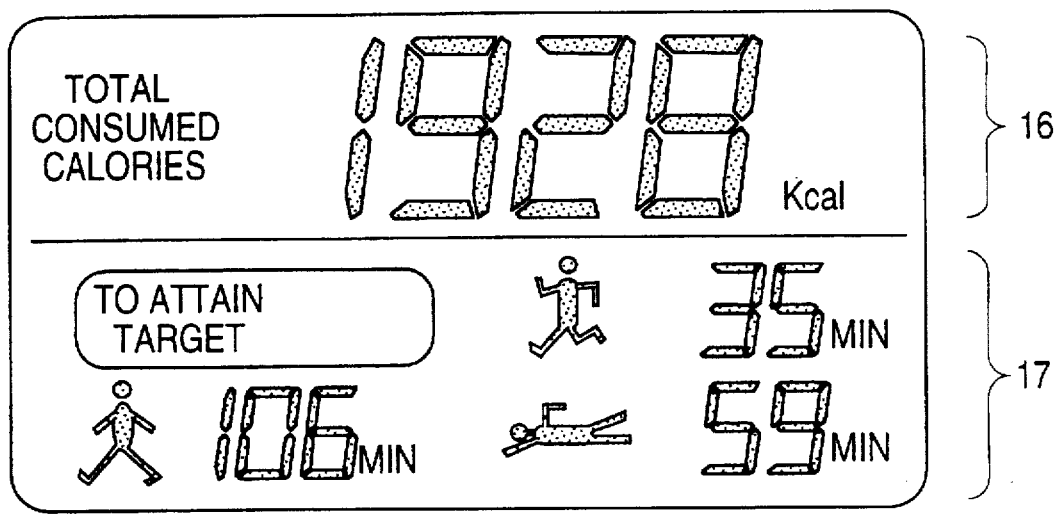
FIGS. 9A and 9B show still another example of a display form in the first embodiment.
Figure 9B:
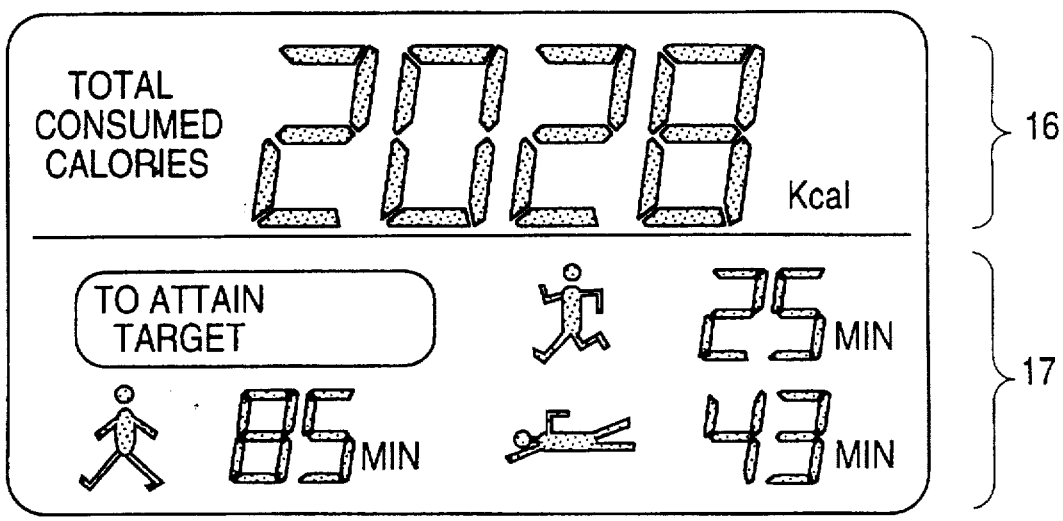

FIGS. 9A and 9B show still another example of a display form. According to this display form, target consumption calories and total consumed calories are indicated in an upper portion 16 and an exercise time necessary to reach the target consumption calories is indicated in a lower portion 17. As in the above example, once a gender, age, height and weight are input, target calories suitable for that person are set and displayed. A display of FIG. 9A indicates that at time point when 1,928 kcal has been consumed, walking of 106 minutes, running of 35 minutes, or swimming of 59 minutes is further needed to attain the target consumption calories. At a time point when 2,028 kcal has been consumed as a result of performing one of the above types of exercise, it is indicated, as shown in FIG. 9B, that walking of 85 minutes, running of 25 minutes, or swimming of 43 minutes is further needed to attain the target consumption calories. A user can easily recognize what amount of exercise he should perform, because the exercise time necessary to reach the target consumption calories decreases as he consumes calories, as described above. Although the example of FIGS. 9A and 9B includes the three types of exercise, i.e., walking, running and swimming, the invention is not limited to such a case but more types of exercise may be indicated. For example, if necessary, bicycle riding, or play of a ball game such as tennis, soccer or baseball may be added.

Figure 10:
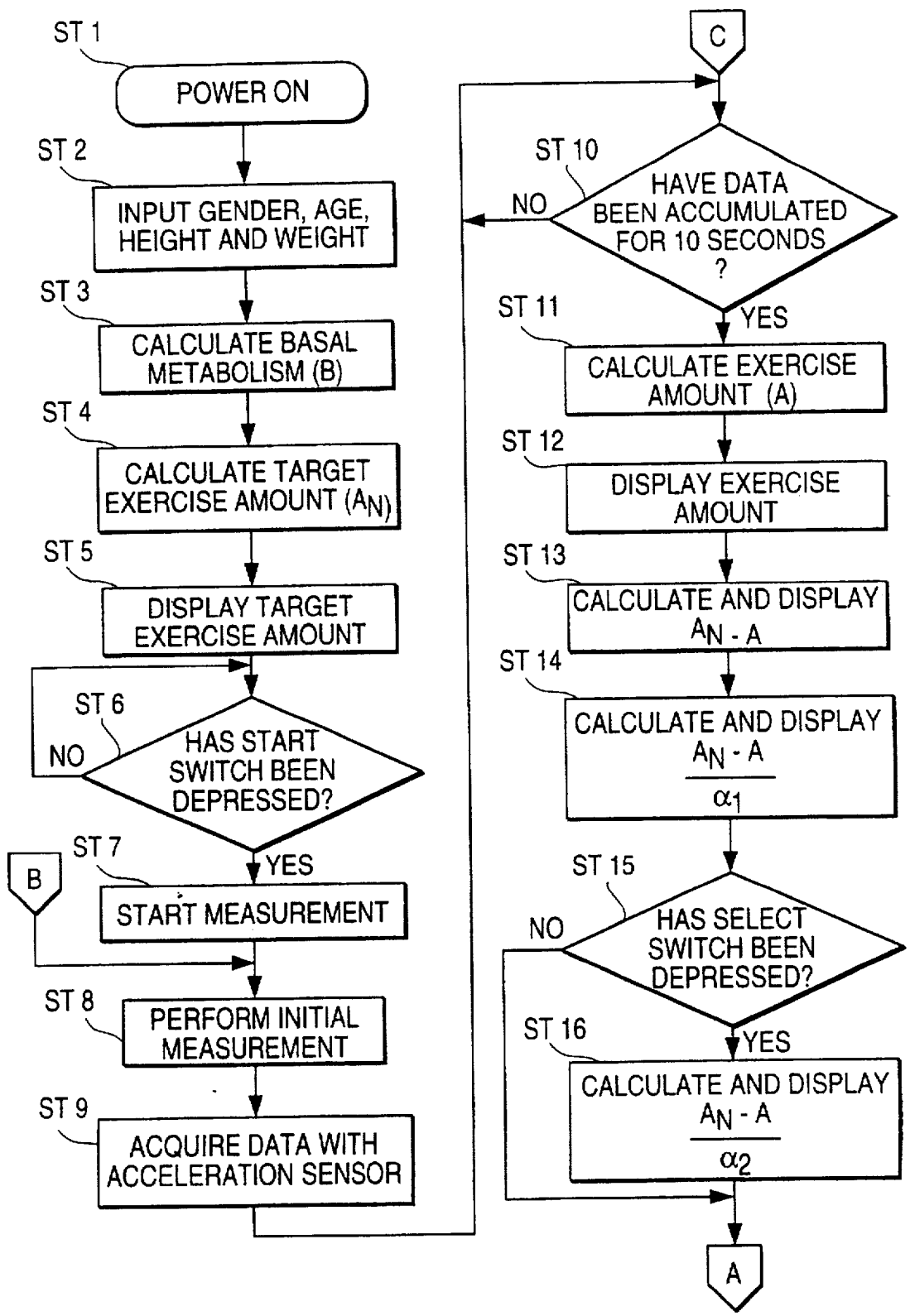
FIGS. 10 and 11 are a flowchart showing the overall operation of the exercise amount measuring device of the first embodiment.
Figure 11:
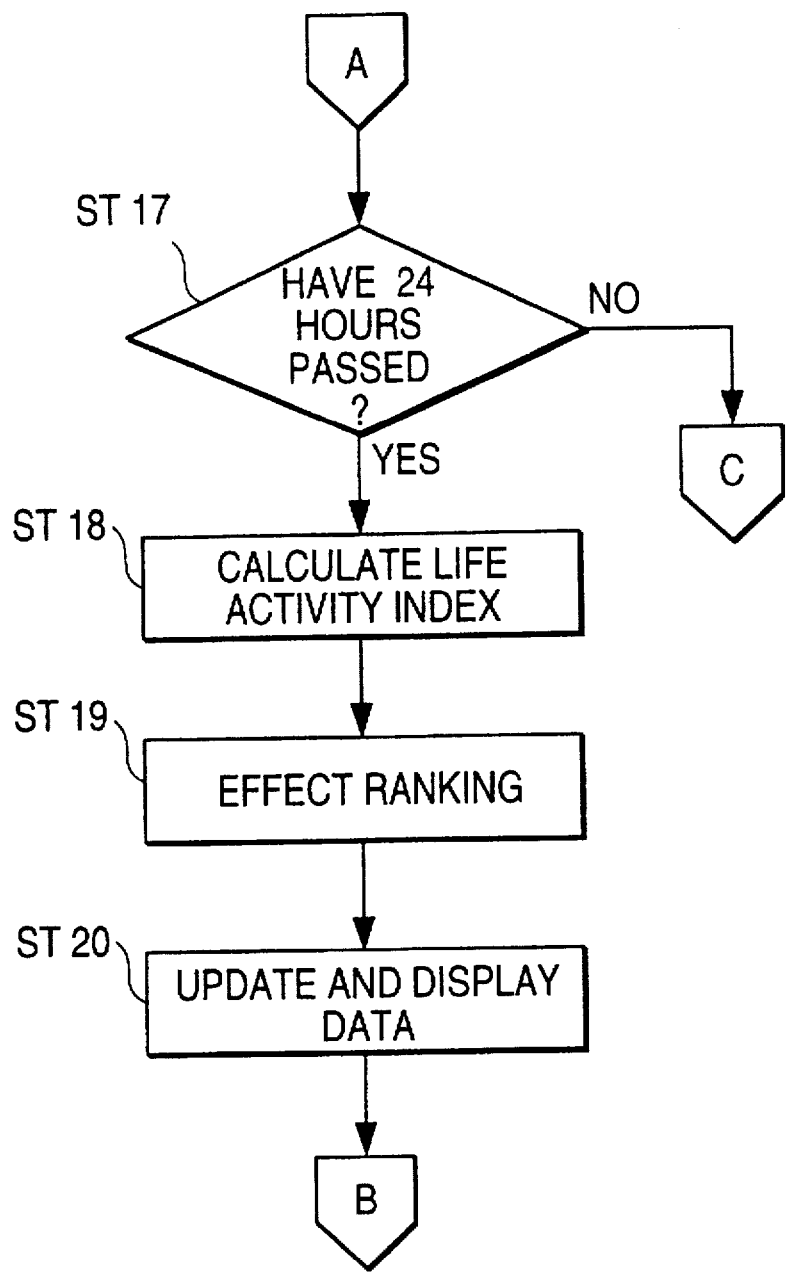

Next, an example of overall operation of the above exercise amount measuring device will be described with reference to a flowchart of FIGS. 10 and 11. After the power of the device is turned on in Step (hereinafter abbreviated as "ST") 1, a gender, age, height and weight of a subject person is input (ST 2). As a result, a basal metabolism B is calculated, for instance, according to Equation (1) (ST 3). Then, a target exercise amount $A_N$ is calculated according to Equation (4) using the calculated basal metabolism B (ST 4), and displayed on the display 5 in the manner described above (ST 5). In ST 6, it is judged whether a measurement start switch has been depressed. If the judgment result is negative, waiting is effected until the start switch is depressed. If the judgment result is affirmative, a measurement is started (ST 7). It goes without saying that the device should be mounted on the subject person before the measurement.

Upon the start of the measurement, an initial measurement is performed (ST 8) and data of a body movement of the subject person is acquired with the acceleration sensor 1 (ST 9). In ST 10, it is judged whether acquired data have been accumulated for 10 seconds. If the judgment result is negative, the data acquisition with the acceleration sensor 1 is continued. If the judgment result is affirmative, an exercise amount A is calculated according to Equation (2) (ST 11) and displayed (ST 12).

Subsequently, a difference ($A_N$–A) between a target exercise amount $A_N$ and the measured exercise amount A is calculated and displayed (ST 13), and ($A_N$–A)/$\alpha_1$ is calculated and displayed (ST 14), where $\alpha_1$, is a constant 3.5 kcal/min for walking. The calculation of ($A_N$–A)/$\alpha_1$, is to determine a remaining time of walking that is needed to reach the target exercise amount $A_N$. In ST 15, it is judged whether the select switch has been depressed. If the judgment result is affirmative, ($A_N$–A)/$\alpha_2$ is calculated and displayed (ST 16), where $\alpha_2$ is a constant 5 kcal/min for running. A remaining time of running needed is determined by this calculation.

In ST 17, it is judged whether 24 hours (one day) have passed from the measurement start. If the judgment result is negative, steps 9–17 are repeated. If the judgment result is affirmative, a life activity index $\chi$ is calculated according to Equation (3) (ST 18), and classified as a particular rank based on the preset data for classifying the life activity index and the life activity intensity (ST 19). In ST 20, the 24-hour data is updated, and the total exercise amount (i.e., total consumed calories) and the life activity intensity (activity intensity), etc. of the 24 hours are displayed. Then, the process returns to the initial measurement step (ST 8) to start acquisition of next 24-hour data. It goes without saying that the 24-hour data is stored in the memory.

Embodiment 2

Referring to FIG. 1, an exercise amount measuring device of this embodiment is different from that of the first embodiment in the following points. That is, a MPU 4' has a function of calculating an exercise amount based on the received digital signal, a function of classifying an action of a living body by recognizing the pattern of an output waveform obtained by the acceleration sensor 1, calculating a consumed energy for each action type, and calculating a total consumed energy from the calculated consumed energies, and other functions. A display (display section ) 5' displays a gender, age, (total) consumed calories, etc.

Figure 12:
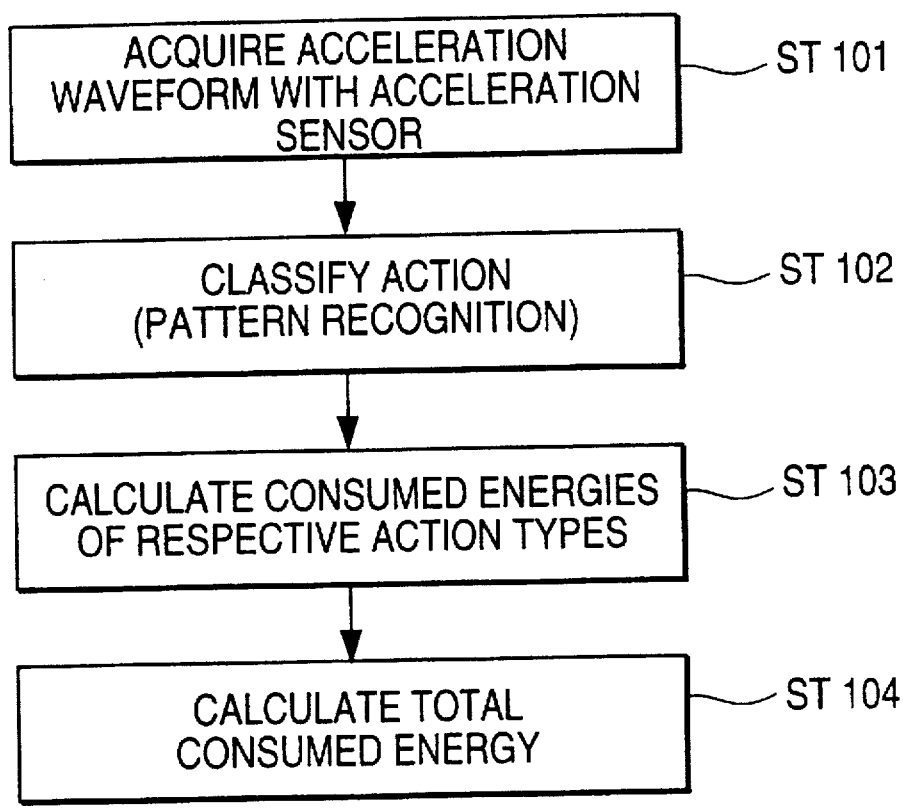
FIG. 12 is a general flowchart showing how to calculate a total consumed energy in the exercise amount measuring device according to the second embodiment of the invention.

FIG. 12 is a general flowchart showing a process of calculating a total consumed energy (calories) in the above exercise amount measuring device. First, in Step (hereinafter abbreviated as "ST") 101, an acceleration waveform is obtained with the acceleration sensor 1 that is mounted on a subject person. In ST 102, the pattern of the obtained acceleration waveform is recognized and an action is classified. In ST 103, a consumed energy of each classified action type is calculated according to a prescribed equation (described later). In ST 104, the consumed energies thus calculated are summed up to determine a total consumed energy.

Figure 13:
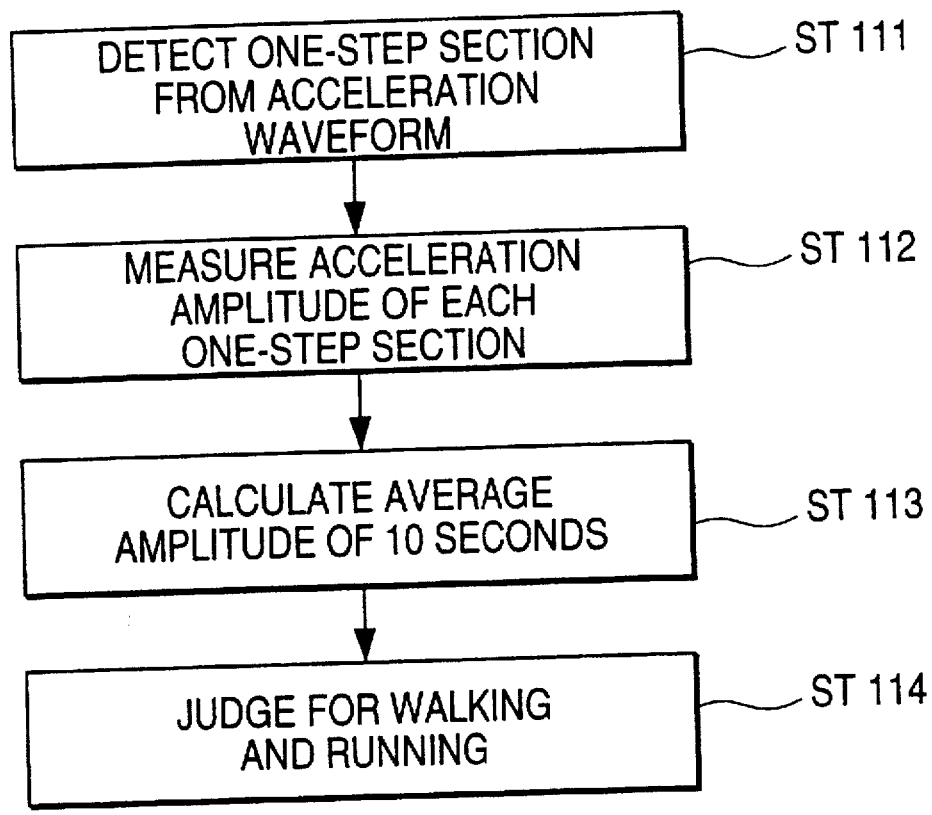
FIG. 13 is a flowchart showing a judgment algorithm for walking and running used in classifying action types.
Figure 14A:
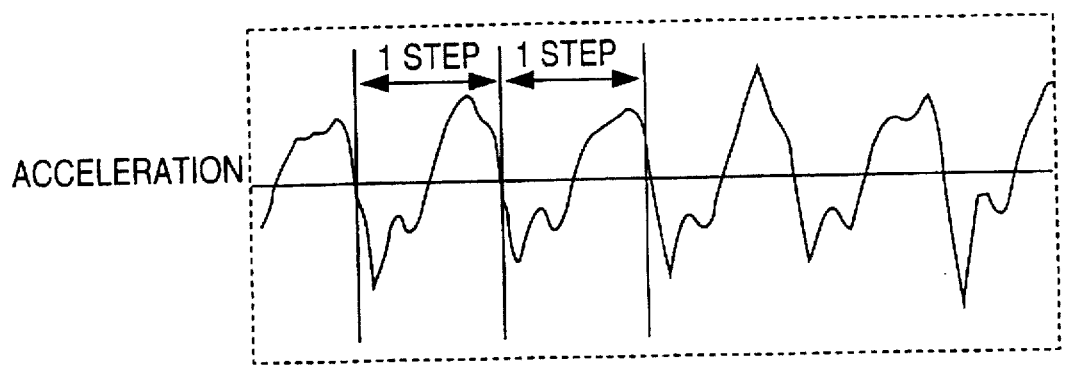
FIGS. 14A and 14B show acceleration waveforms illustrating the judgment algorithm for walking and running.
Figure 14B:
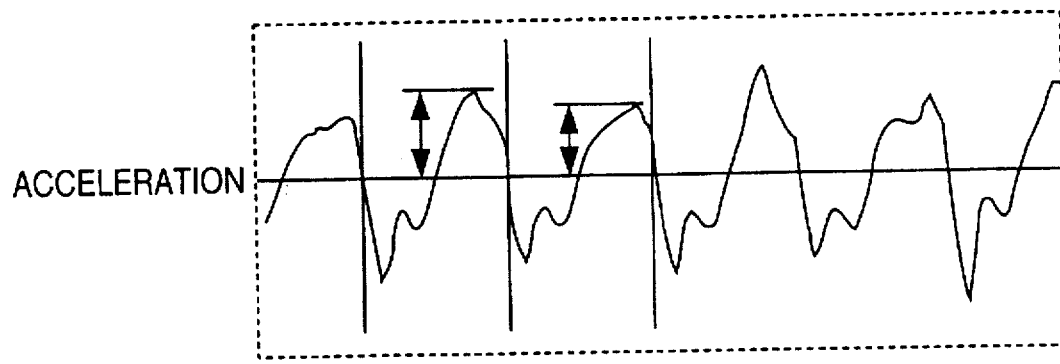

The classification of respective actions in ST 102 will be described in detail for a case of using five types of action, i.e., sleeping, sitting, standing, walking and running. FIG. 13 shows a judgment algorithm for walking and running. Referring to FIG. 13, in ST 111, one-step section is detected from the acceleration waveform (see FIG. 14A). In ST 112, an acceleration amplitude of the one-step section is measured as shown in FIG. 14B, where acceleration amplitudes are represented by $VP_1, VP_2, \ldots, VP_n$. In ST 113, an average amplitude $VP_{mean}$ over 10 seconds from the measurement start is calculated according to the following equation.

$$VP_{mean}=(VP_1+VP_2+ \ldots +VP_n)/n$$

In ST 114, the judgment for walking or running is made based on the value of $VP_{mean}$. That is, the action is judged to be walking if $VP_{mean} \leq VP_{th}$, and running if $VP_{mean} > VP_{th}$.

Figure 15A:
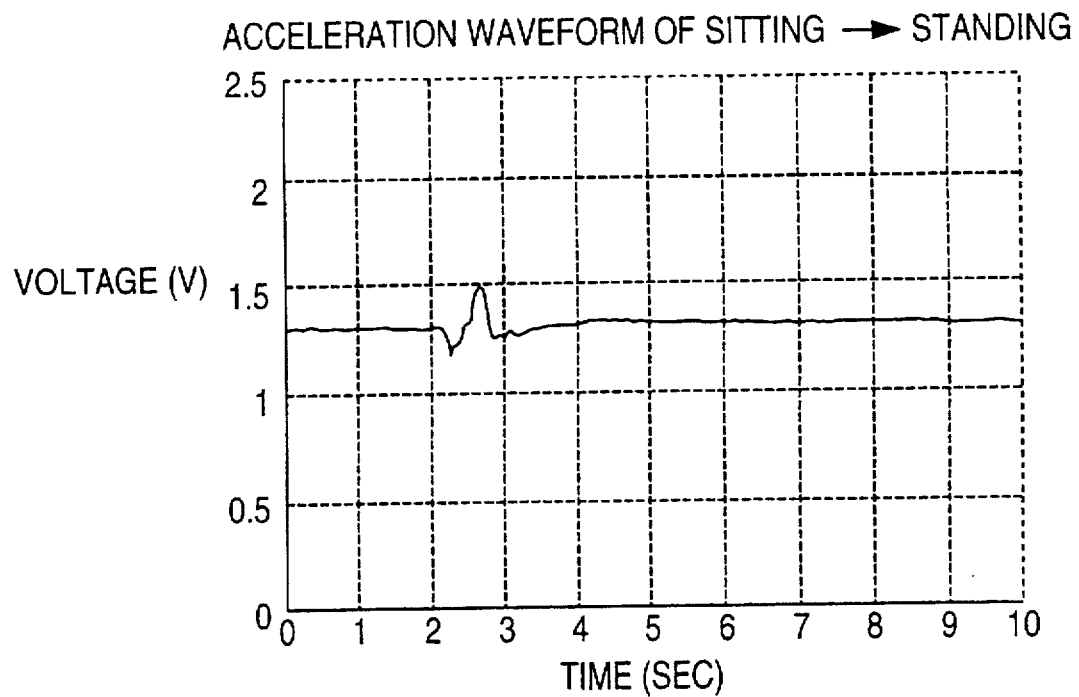
FIGS. 15A and 15B show acceleration waveforms illustrating a judgment algorithm for sitting and standing used in classifying action types.
Figure 15B:
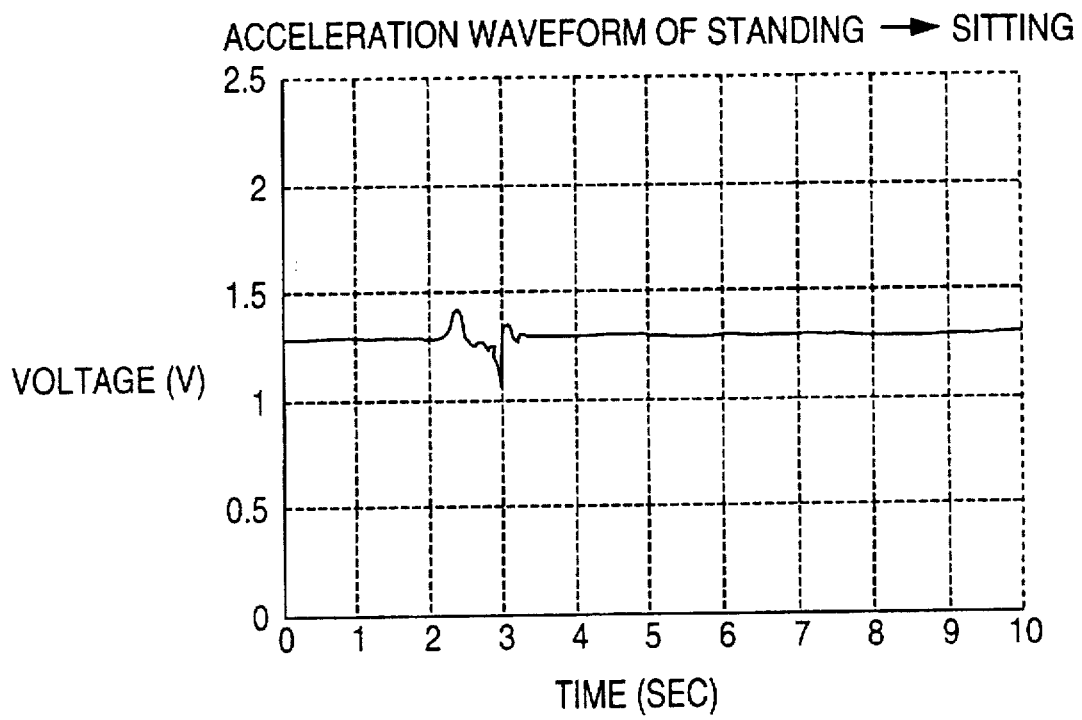

A judgment algorithm for sitting and standing will be described with reference to FIGS. 15A and 15B. FIG. 15A shows an acceleration waveform that is obtained when a subject person changes his action from sitting to standing. In this case, downward acceleration appears first and then upward acceleration appears in the acceleration waveform. FIG. 15B shows an acceleration waveform that is obtained when a subject person changed his action from standing to sitting. In this case, upward acceleration appears first and then downward acceleration appears in the acceleration waveform. Therefore, discrimination between sitting and standing can be made by detecting the above differences in waveform. When there occurs no change in an acceleration waveform that is supplied from the acceleration sensor 1 for a prescribed period (for instance, one hour), the action is judged to be sleeping because a subject person is kept still or quiet.

A basal metabolism is needed to calculate a consumed energy of each discriminated action type. One of various methods for determining the basal metabolism is described in the first embodiment (Equation (1)).

In addition to the basal metabolism, a RMR (relative metabolic rate) is needed which represents a ratio of the amount of metabolism with a certain exercise to the basal metabolism, and calculated as $$RMR = \{(\text{total amount of metabolism with activity}) -$$

$$(\text{amount of quiet-state metabolism})\}/(\text{basal metabolism}).$$

The following results are derived from this equation:
Sitting state: RMR 0.34
Standing state: RMR=0.8 (male), 0.98 (female)
Walking state: RMR=$\alpha_0$+$\alpha_1$×height+$\alpha_2$×(walking pace)
(For instance, RMR=2.3.)
Running state: RMR=$\alpha_0$+$\alpha_1$×weight+$\alpha_2$×(acceleration amplitude)
(For instance, RMR=3.8.)
In the above equations, $\alpha_0$, $\alpha_1$ and $\alpha_2$ are constants determined experimentally. In a sleeping state, RMR=0.3, for instance.

An energy metabolism (total consumed calories) in a prescribed period (one day) is calculated according to the following equation:

$$E_{day}=\Sigma\{(RMR_i+1.2) \times T_i\} \times B+0.9 \times T_O \times B$$

where
$RMR_i$: energy metabolic rate of a certain exercise
$T_i$: period of the certain exercise (hour)
$T_O$: sleeping period (hour)
B: basal metabolism (kcal/hour).

Here, "a certain exercise" is one of action types including sitting, standing, walking and running. The sum of consumed energy of each action type is determined according to the above equation, and a total consumed energy is calculated based on those sums.

Figure 16:
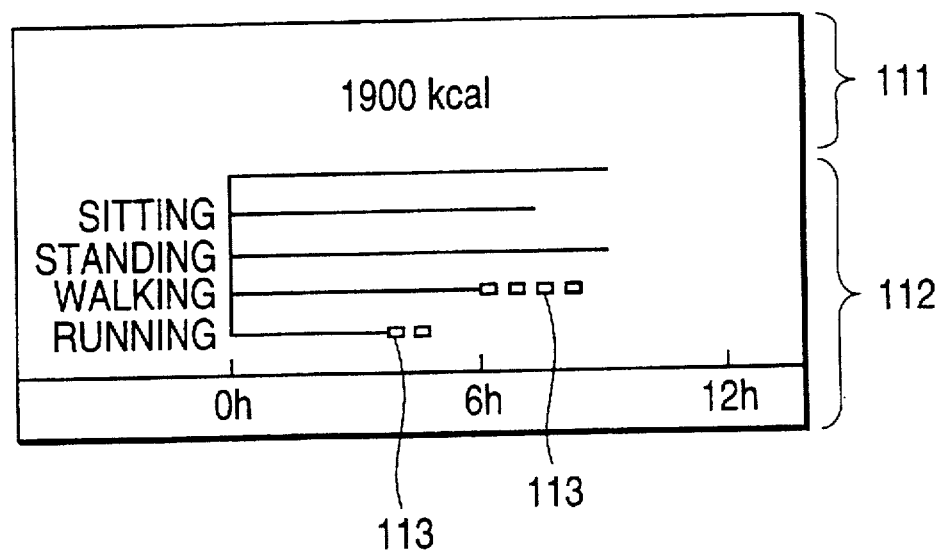
FIGS. 16 and 17 show examples of display forms of the exercise amount measuring device according to the second embodiment of the invention.

Next, a description will be made of a display form of the display screen of the display 5'. In an example shown in FIG. 16, the display screen is divided into an upper portion 111 and a lower portion 112. Total consumed calories (kcal) are indicated in the upper portion 111 as a numerical value, and periods of the respective action types (sitting, standing, walking and running), i.e., time ratios of the respective life activity types are indicated by a bar graph in the lower portion 112. In this example, the horizontal axis is marked in a time scale and periods are indicated so as to be accumulated for the respective action types. Further, marks 113 included in the bars for walking and running are, for instance, flashed to indicate that those exercises were performed alternately. Alternatively, life activity indices (or life activity intensities) may be displayed.

The life activity index is calculated in the same manner as in the first embodiment according to the following equation (Equation (3)):

$$\chi = 0.9(A/B) - 1.$$

Thus, the life activity index $\chi$ can be determined based on the total energy metabolism A and the basal metabolism B. It is possible to inform a user of the level of an action by classifying the life activity index into four ranks so that they are associated with respective life activity intensities.

Figure 17:
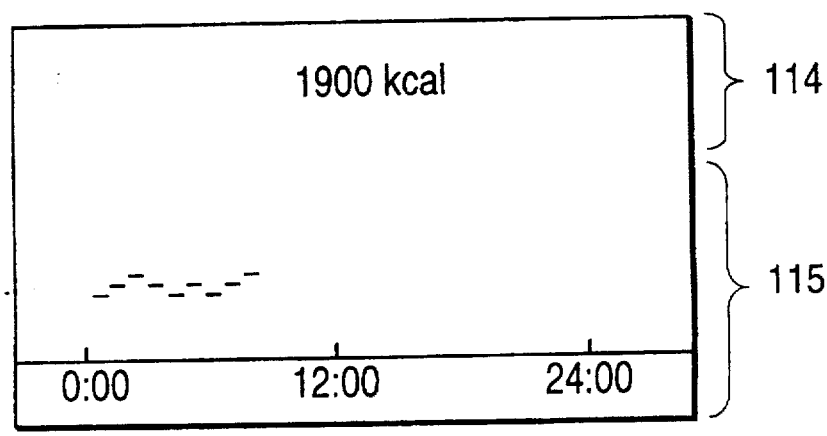

In another display form shown in FIG. 17, total consumed calories (kcal) are indicated in an upper portion 114 and an activity pattern over time is indicated in a lower portion 115. The horizontal axis is marked in a time scale, and activity levels are indicated in two-hour sections over a predetermined period (0:00 to 24:00). The vertical axis is marked in a scale of calories, the number of steps, the exercise amount, or the like. It goes without saying that activity levels may be indicated in one-hour sections over 12 hours. The device may be adapted to switch between the above two modes of time representation with the select switch or some other switch. The 24-hour representation has an advantage that a user can recognize his activity pattern of one day at a glance, while he can recognize his activity pattern more precisely by the 12-hour representation. This display form allows a user to recognize a temporal variation of his activity levels at a glance.

Figure 18:
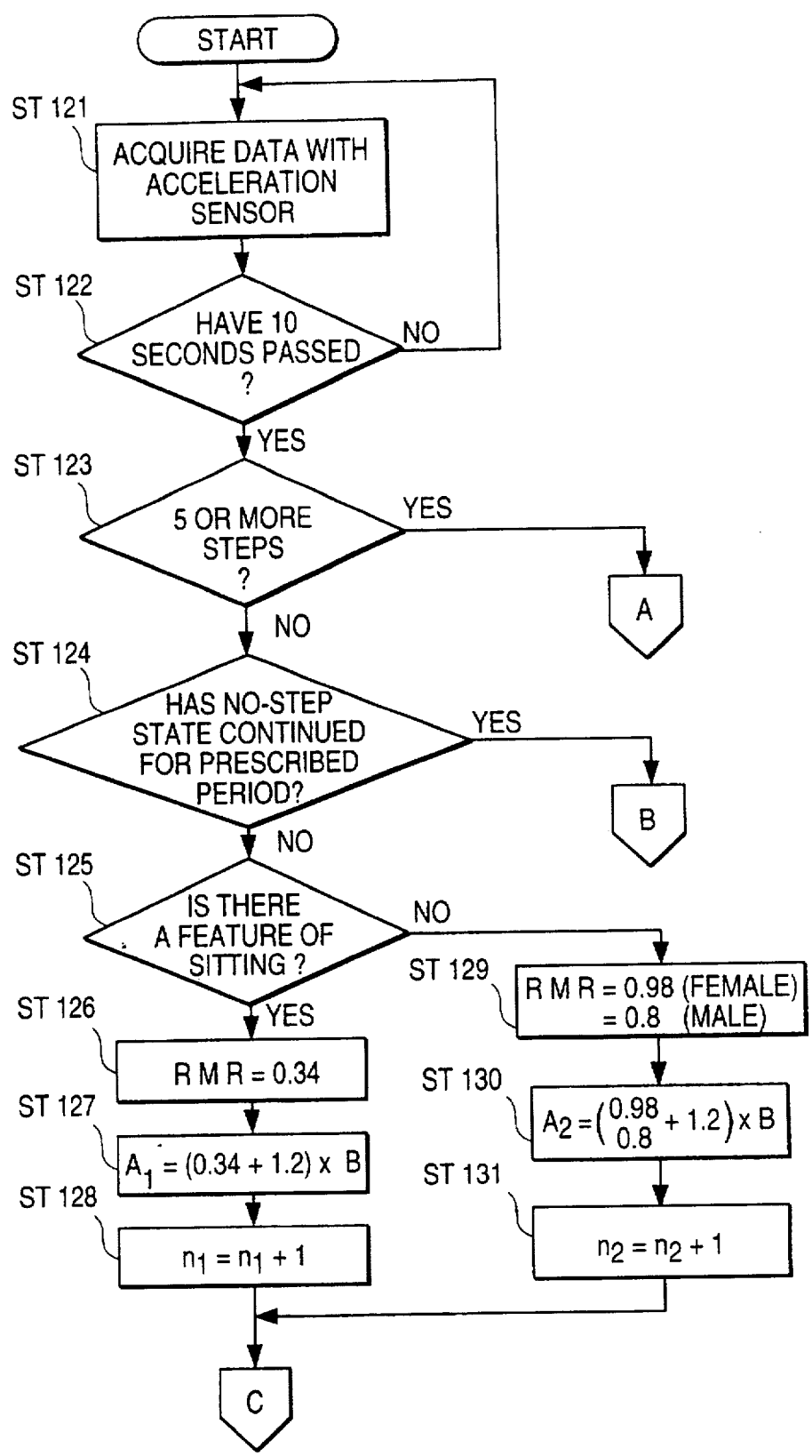
FIGS. 18 and 19 are a flowchart showing the entire operation of the exercise amount measuring device according to the second embodiment.
Figure 19:
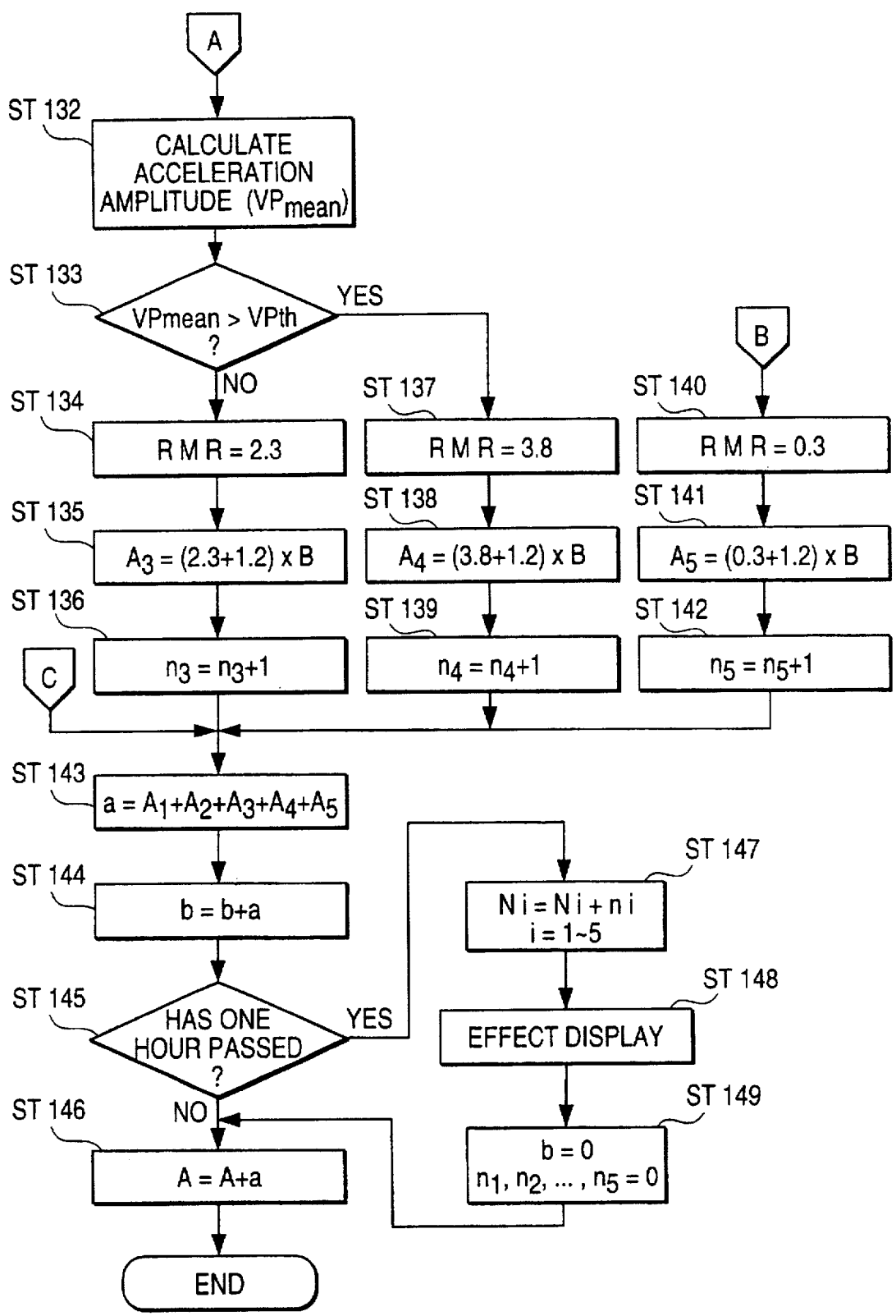

Next, with reference to a flowchart of FIGS. 18 and 19 a description will be made of an example of the entire operation of the above exercise amount measuring device. When the power of the device is turned on, a measurement is started and data relating to a body movement of a subject person are acquired with the acceleration sensor 1 (ST 121). It goes without saying that prior to the measurement, the device has been mounted on the subject person and his gender, age, height and weight have been input. In ST 122, it is judged whether 10 seconds have passed from the measurement start. If the judgment result is negative, the data acquisition with the acceleration sensor 1 is continued to store data of 10 seconds.

If the judgment result in ST 122 is affirmative, it is then judged whether an exercise of 5 or more steps has been performed (ST 123). If the judgment result is affirmative, the process goes to ST 132 for calculating an acceleration amplitude (described later). That is, based on the fact that the action includes 5 or more steps, it is judged that the action should be walking or running. And the process goes to steps therefor. If the judgment result in ST 123 is negative, it is then judged in ST 124 whether a no-stepping state (still or quiet) has continued for a prescribed period. If the judgment result in ST 124 is affirmative, it is judged that the subject person has not moved for the prescribed period and therefore this action is sleeping. The process goes to ST 140 for sleeping.

If the judgment result in ST 124 is negative, it is then judged in ST 125 whether the action includes the feature of sitting in the manner described in connection with FIGS. 15A and 15B. If the judgment result in ST 125 is affirmative, the action is judged to be sitting. Otherwise, the action is judged to be standing. The process goes to ST 126 or 127 for either case.

In the steps for sitting, RMR is set at 0.34 as described above (ST 126). In ST 127, a consumed energy $A_1$ of sitting in a prescribed period (10 seconds) is calculated according to the equation for calculating the energy metabolism (total consumed calories) $E_{day}$. After a number $n_1$ for sitting is incremented by one (ST 128), the process goes to ST 143.

In steps for standing, RMR is set at 0.98 (for female) or 0.8 (for male) in ST 129, a consumed energy $A_2$ of standing is calculated in the same manner (ST 130). After a number $n_2$ for standing is incremented by one (ST 131), the process goes to ST 143.

In ST 132, an average acceleration amplitude $VP_{mean}$ is calculated in the above-described manner. In step ST 133, it is judged whether the calculated average amplitude $VP_{mean}$ is larger than a prescribed value $VP_{th}$. If the judgment result is negative (i.e., $VP_{mean} \leq VP_{th}$), the action is judged to be walking. Otherwise, the action is judged to be running.

In steps for walking, RMR is set at 2.3 (ST 134) and a consumed energy $A_3$ is calculated (ST 125). After a number $n_3$ for walking is incremented by one (ST 136), the process goes to ST 143.

In steps for running, RMR is set at 3.8 (ST 137) and a consumed energy $A_4$ is calculated (ST 138). After a number $n_3$ for running is incremented by one (ST 139), the process goes to ST 143.

On the other hand, in steps for sleeping, RMR is set at 0.3 (ST 140) and a consumed energy $A_5$ is calculated (ST 140). After a number $n_4$ for sleeping is incremented by one (ST 142), the process goes to ST 143.

In ST 143, a consumed energy a of this period (10 seconds) is calculated according to $a = A_1 + A_2 + A_3 + A_4 + A_5$. In ST 144, the value a is added to a subtotal consumed energy b. In ST 145, it is judged whether one hour has passed. If the judgment result is negative, the consumed energy a of 10 seconds is added to a total consumed energy A (ST 146). Thus, the process of this 10-second period is completed.

If the judgment result in ST 145 is affirmative, a total number of actions of each action type is calculated according to $N_i = N_i + n_i$ (i=1 to 5) in ST 147, and the results are displayed in ST 148. After the subtotal consumed energy b and the numbers $n_1 - n_5$ are reset to 0 (ST 149), the consumed energy a of this 10-second period is added to the total consumed energy A (ST 146), to complete the process. As the above process is repeated for each 10 seconds, the various data are sequentially stored into the memory.

Embodiment 3

Referring to FIG. 1, an exercise amount measuring device of this embodiment is different from that of the first embodiment in the following points. That is, a MPU 4" has a function of calculating estimated consumption calories in a predetermined period (for instance, one day), a function of comparing ingested calories and consumed calories in the predetermined period (one day) and determining advice based on the comparison result, a function of calculating a difference between ingested calories and consumed calories in the predetermined period (one day) and determining a tendency of whether a user is gaining or losing weight based on the calculated difference, and other functions. A display (display section) 5" displays a gender, age, consumed calories (exercise amount), ingested calories (amount of ingested food), various kinds of advice etc.

The exercise amount measuring device of this embodiment calculates consumed calories, ingested calories, a difference therebetween, and other parameters by the various calculating functions. To this end, a basal metabolism is needed to calculate a consumed energy of each discriminated action type. One of various methods for determining the basal metabolism is described in the first embodiment (Equation (1)).

On the other hand, a necessary exercise amount is expressed as a difference between ingested calories and consumed calories:

(necessary exercise amount)=(ingested calories)−(consumed calories).

Further, an energy metabolism $E_{act}$ with a certain exercise is represented by $$E_{act}=(RMR+1.2) \times T_{act} \times B \quad (5)$$

where

RMR: relative metabolic rate with the exercise
$T_{act}$: exercise time
B: basal metabolism.

With an assumption that the basal metabolism B is calculated in advance according to Equation (1) based on a gender, age, height and weight, the necessary exercise time $T_{act}$ can be determined from Equation (6) (a modified version of Equation (5) if the type of exercise (i.e., RMR) is determined.

$$T_{act}=E_{act}/\{(RMR+1.2) \times B\} \quad (6)$$

The calculation may be performed with RMR set at 2.3 and 3.8 for walking and running, respectively. For example, in the case of a 35-year-old male of 60 kg in weight and 170 cm in height, the basal metabolism B is about 60 kcal/hour. If the ingested calorie value is 1,600 kcal and the consumed calorie value is 1,400 kcal, $$\begin{aligned}(\text{necessary exercise amount}) &= 1{,}600 - 1{,}400 \\ &= 200 \text{ (kcal)}.\end{aligned}$$

According to Equation (6), an exercise time $T_{act}$ to consume 200 kcal ($E_{act}$) thus calculated by running is calculated as follows:

$$T_{act}=200/\{(3.8+1.2) \times 60\} \approx 0.67 \text{ (hour)}$$

That is, 200 kcal can be consumed by running of about 40 minutes.

Next, a description will be made of a display form of the display screen of the display 1. First, in an example shown in FIGS. 20A and 20B, the display screen is divided into an upper portion 210 and a lower portion 211. An exercise amount (total consumed calories; kcal) is indicated in the upper portion 210 as a numerical value. Total ingested calories (kcal) and an ingestion/consumption balance (advice) that has been determined from a result of comparison between ingested calories and consumed calories are indicated in the lower portion 211, the latter being indicated as a picture. While the consumed calories are automatically calculated, the ingested calories are input by means of an ingested calorie input means. Input values of ingested calories are accumulated and stored into the memory to constitute the total calories ingested so far (already-input ingested calories).

Figure 21A:
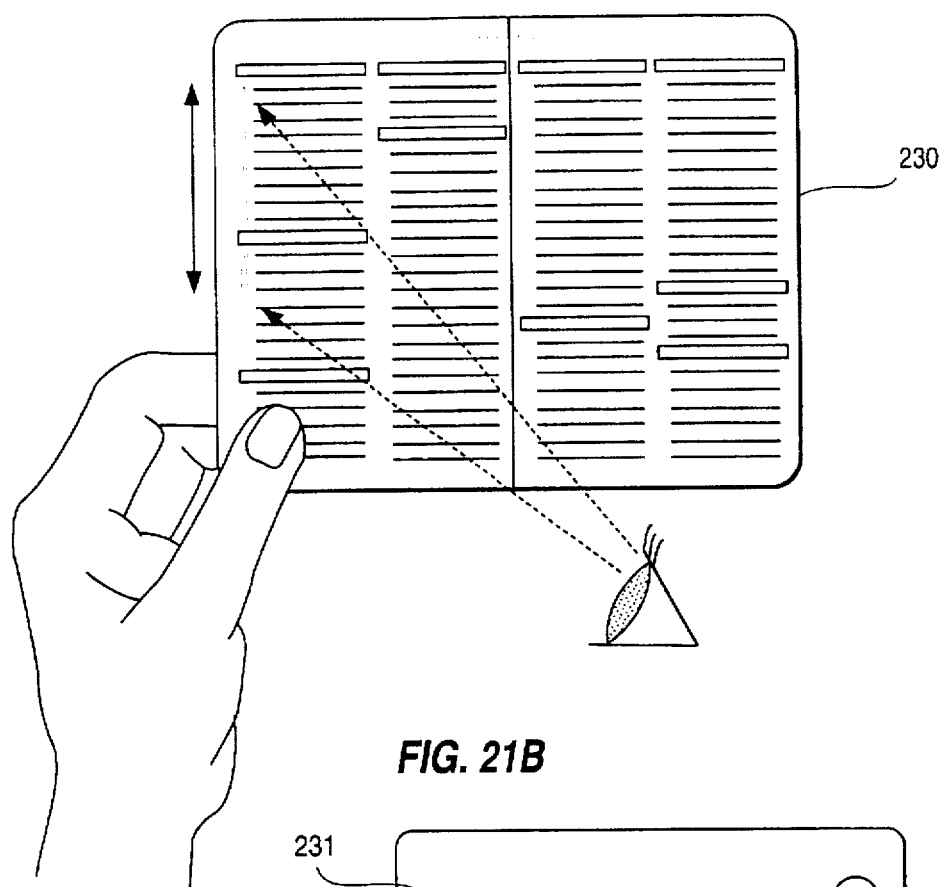
FIGS. 21A and 21B illustrate how to input an ingested calorie value in the third embodiment.
Figure 21B:
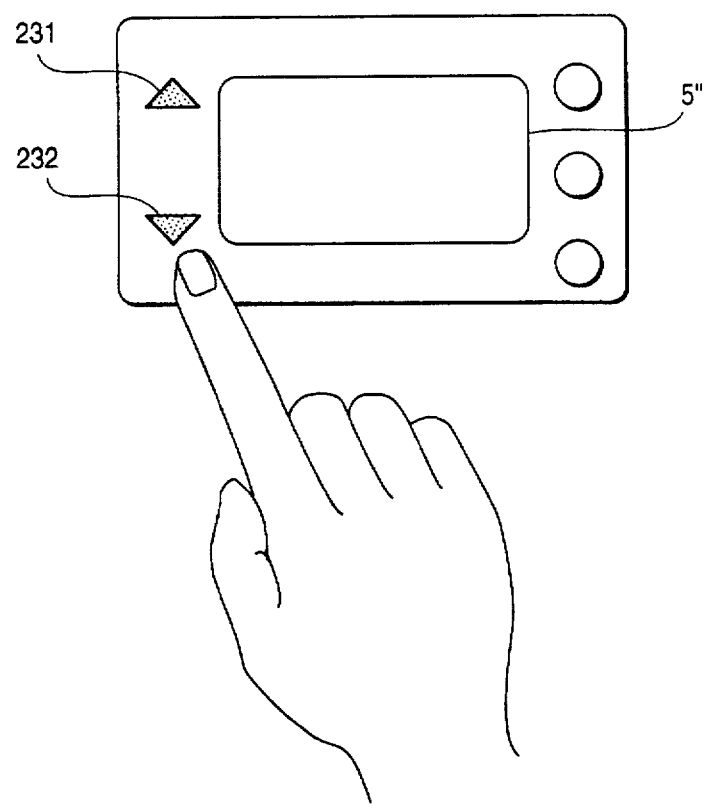

FIGS. 21A and 21B illustrate an example of the ingested calorie input means. FIG. 21A shows a menu sheet 230 on which names of foods and their calories are listed. As shown in FIG. 21B, an up-key 231 and a down-key 232 may be provided at positions spaced sideways from the display screen of the display 5", and a number indicating calories of an ingested food may be selected from the menu sheet 230 and input through the keys 231 and 232. For example, in the case of a food that is not listed on the menu sheet 230, a value of ingested calories may be input directly through the keys.

Figure 20A:
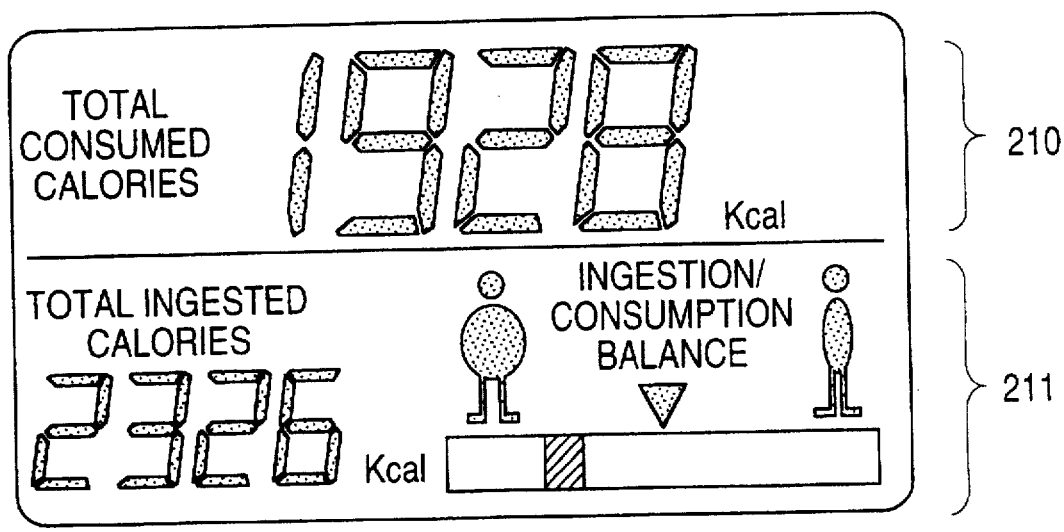
FIGS. 20A and 20B show an example of a display form of the exercise amount measuring device according to the third embodiment of the invention.
Figure 20B:
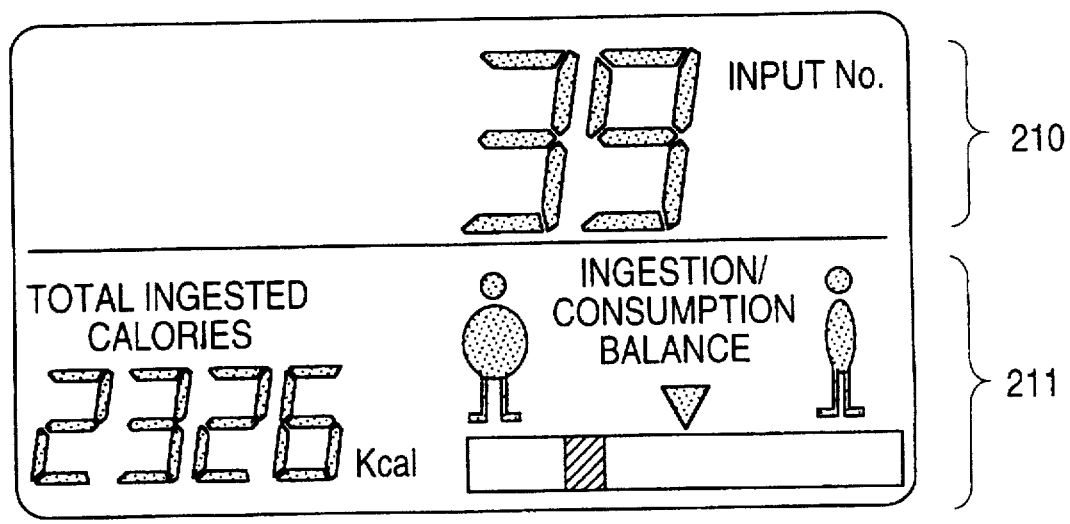

In a case shown in FIG. 20A, the ingested calorie value is 2,326 kcal and the consumed calorie value is 1,928 kcal. Since the ingested calories are larger than the consumed calories, the ingestion/consumption balance indicates a tendency to gaining weight. FIG. 20B shows a case where ingested calories have been input by using a number (39) on the menu sheet 230. By indicating the ingestion/consumption balance in the above manner, a user can recognize, at a glance, a tendency of whether he is gaining or losing weight.

Figure 22A:
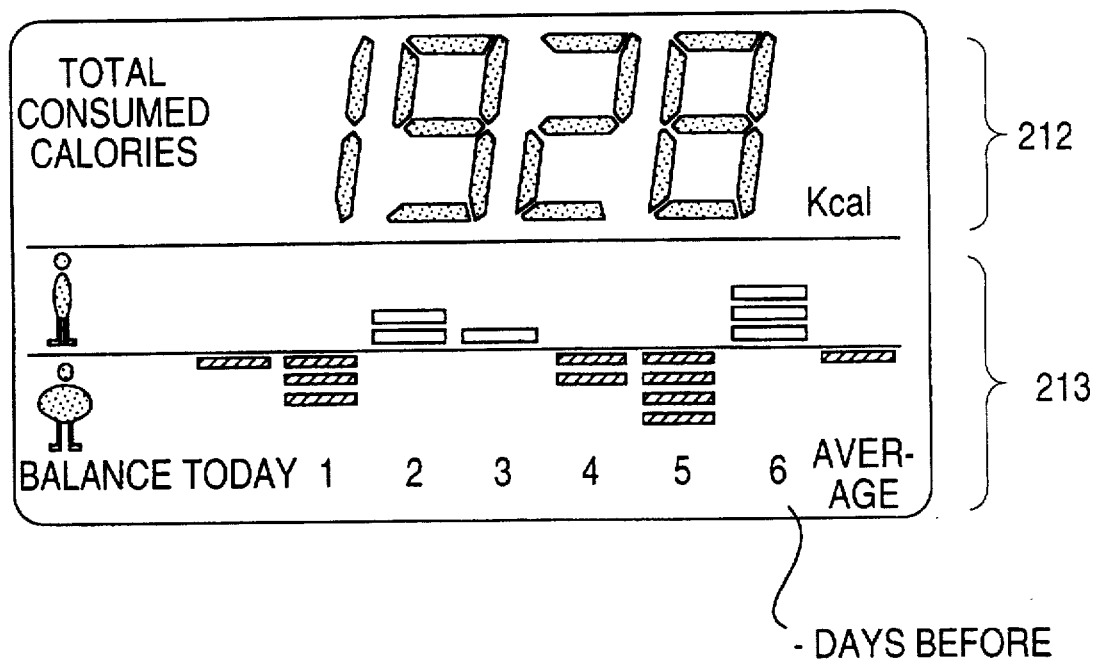
FIGS. 22A and 22B show a modified version of the display form of FIGS. 20A and 20B.
Figure 22B:
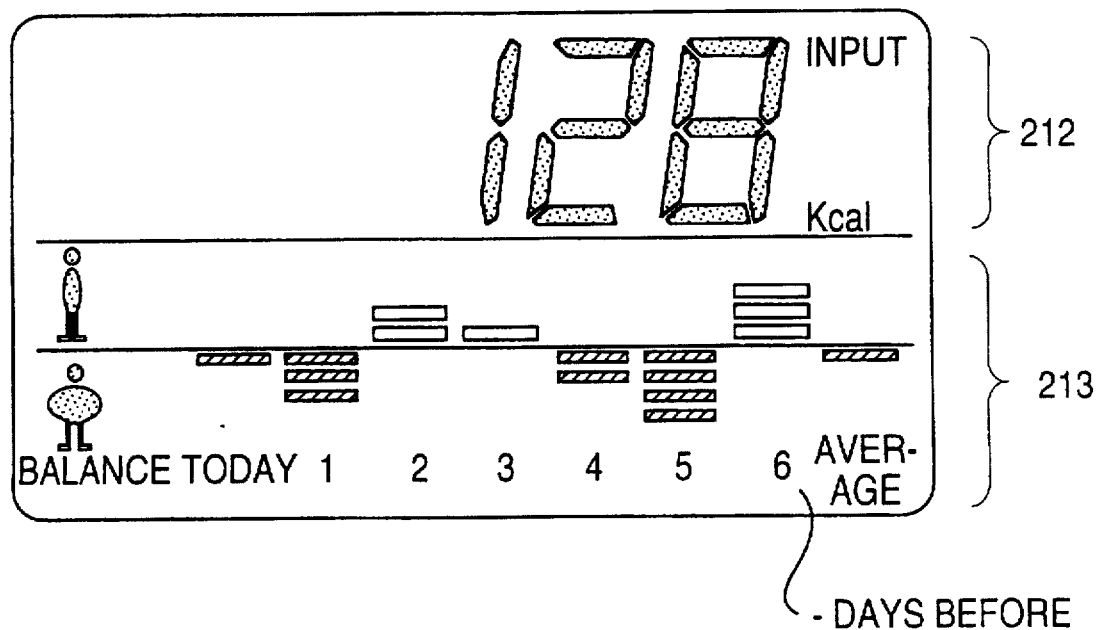

FIGS. 22A and 22B show a modified version of the display form of FIGS. 20A and 20B. In this display form, as in that of FIGS. 20A and 20B, total consumed calories are indicated in an upper portion 212 and an ingestion/consumption balance is indicated in a lower portion 213. As specific features of this display form, the ingestion/consumption balance is indicated by a bar graph, and an ingestion/consumption balance of the present day and each of the past 6 days and an average ingestion/consumption balance of the 7 days (one week) are indicated. To store data of ingestion/consumption balances of 7 days, there may be provided, for instance, an automatic memory function. This display form has an advantage that a user can recognize, at a glance, the ingestion/consumption balances of 7 days and their average balance, and therefore can well understand a tendency of the balances.

Figure 23A:
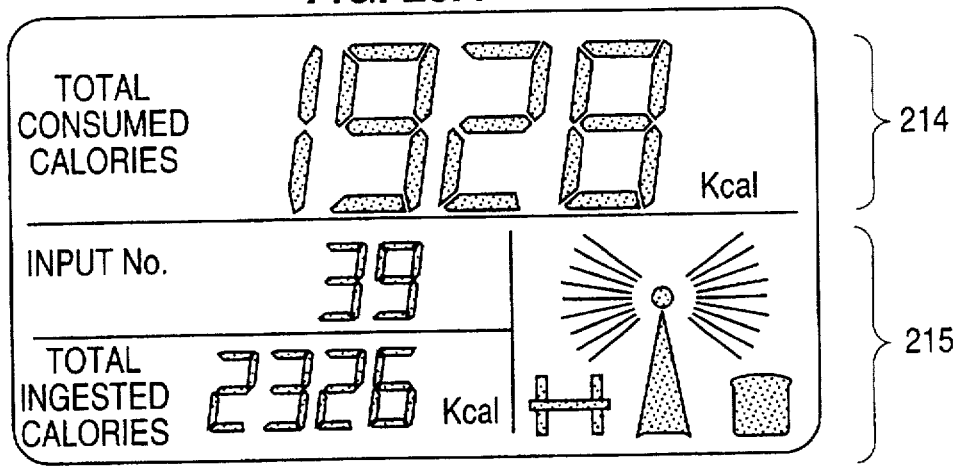
FIGS. 23A–23C show another example of a display form in the third embodiment.
Figure 23B:
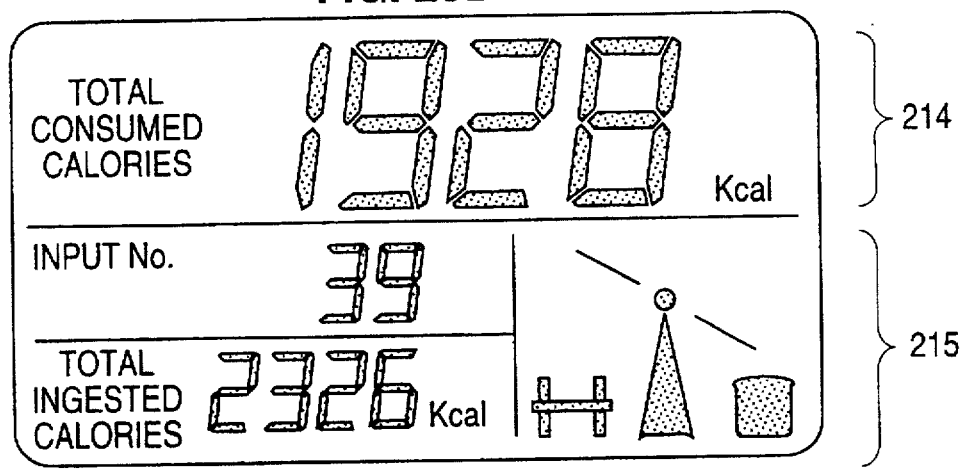
Figure 23C:
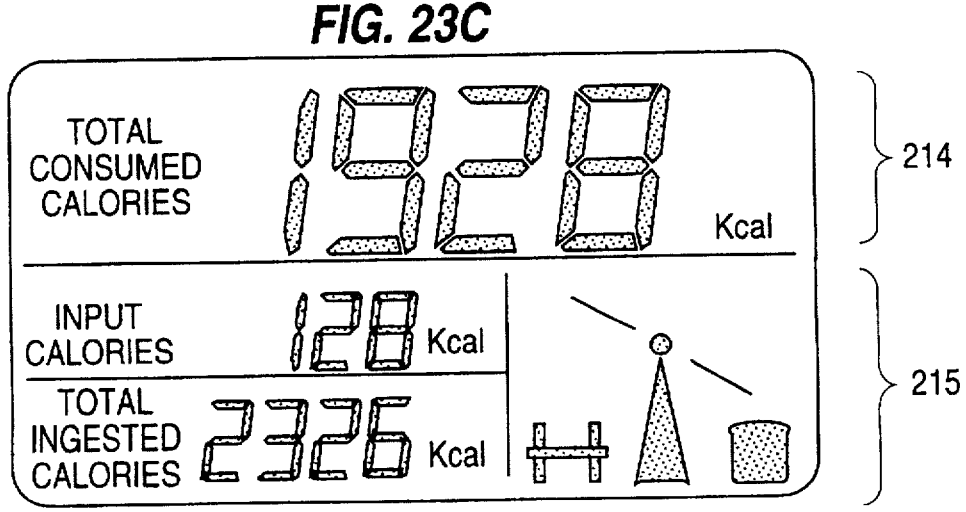

FIGS. 23A–23C show another display form. Also in this display form, total consumed calories are indicated in an upper portion 214 and total ingested calories and an ingestion/consumption balance is indicated in a lower portion 215. In this example, a picture of the ingestion/consumption balance includes marks of a dumbbell and a slice of bread. A seesaw bar inclines to the bread side when the ingested calories are larger, and to the dumbbell side when the consumed calories are larger. Based on the difference between the ingested calories and the consumed calories, FIGS. 23B and 23C indicate that the former is larger than the latter. Further, FIG. 23B indicates that the ingested calories were input by use of a number on the list, and FIG. 23C indicates that the ingested calories were input as a numerical value.

Figure 24A:
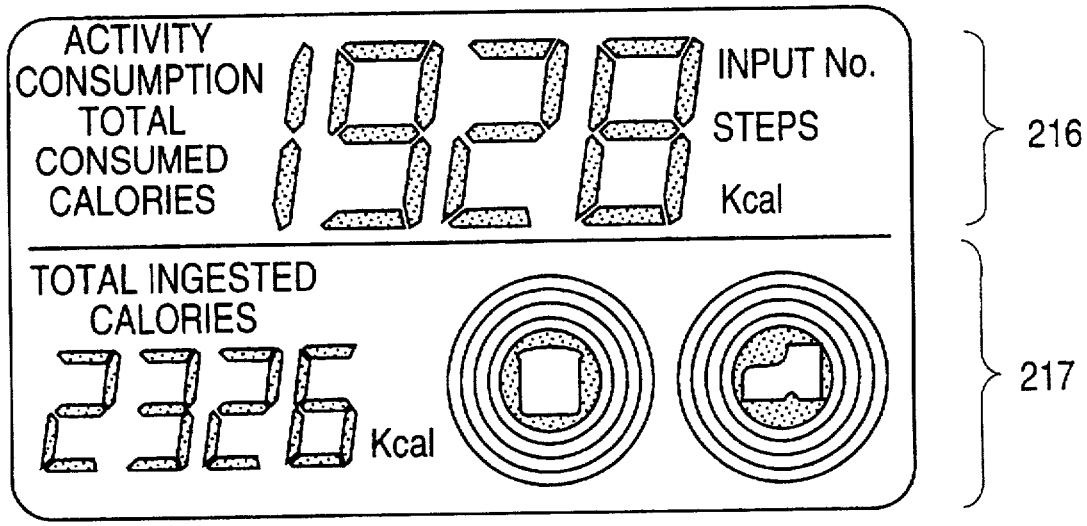
FIGS. 24A and 24B and FIGS. 25A and 25B show still another example of a display form in the third embodiment.
Figure 24B:
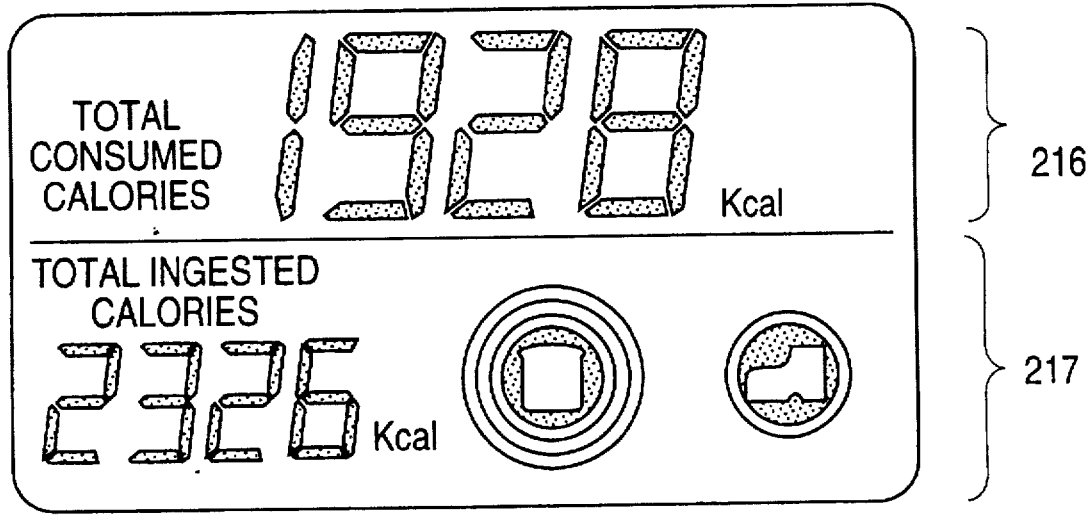
Figure 25A:
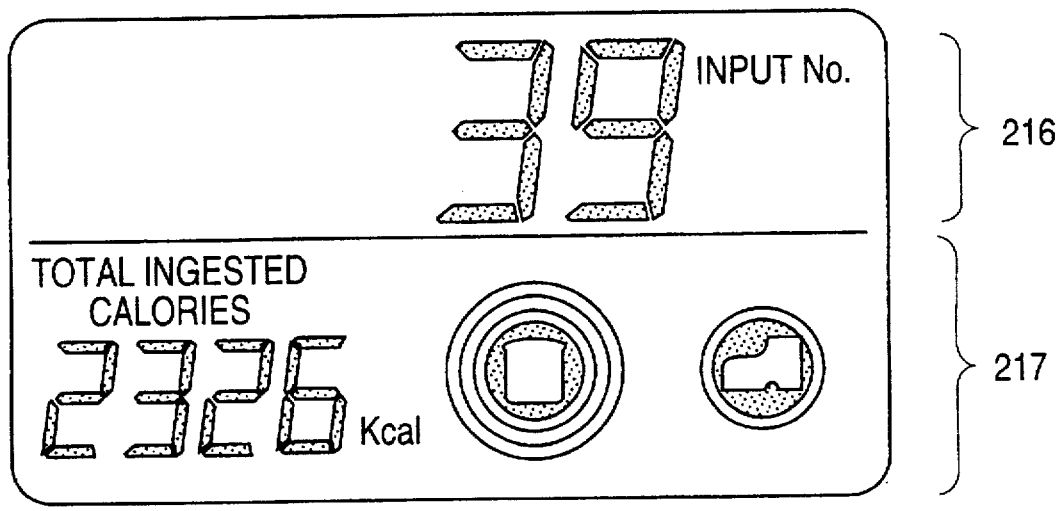
Figure 25B:
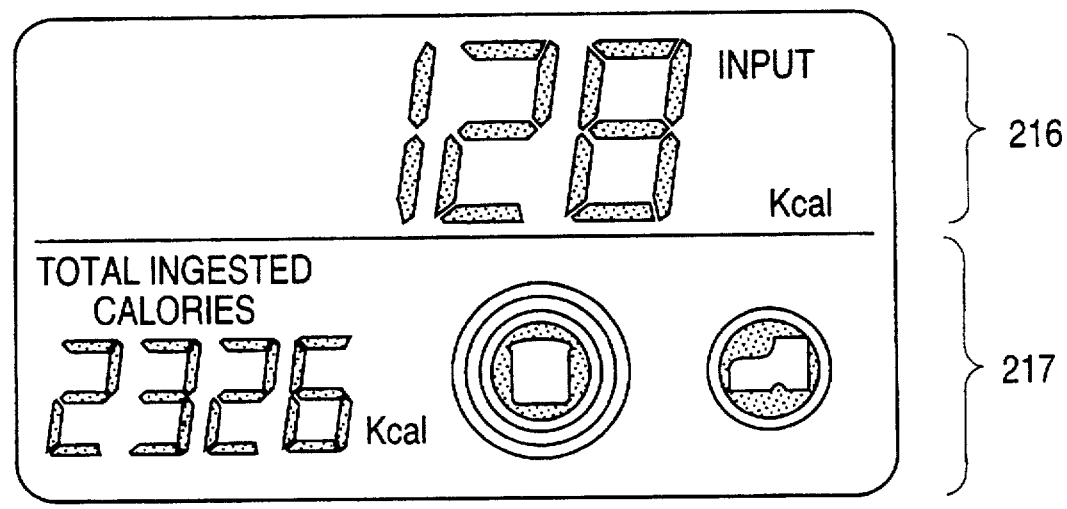

FIGS. 24A and 24B show another display form. In this display form, an ingestion/consumption balance is indicated as concentric circles around each of a shoe and a slice of bread (see FIG. 24A). In a case of FIG. 24B, more circles are drawn around the bread because the ingested calories are larger. FIG. 25A indicates that ingested calories were input by use of a number on the list, and FIG. 25B indicates that ingested calories were input as a numerical value.

Figure 26A:
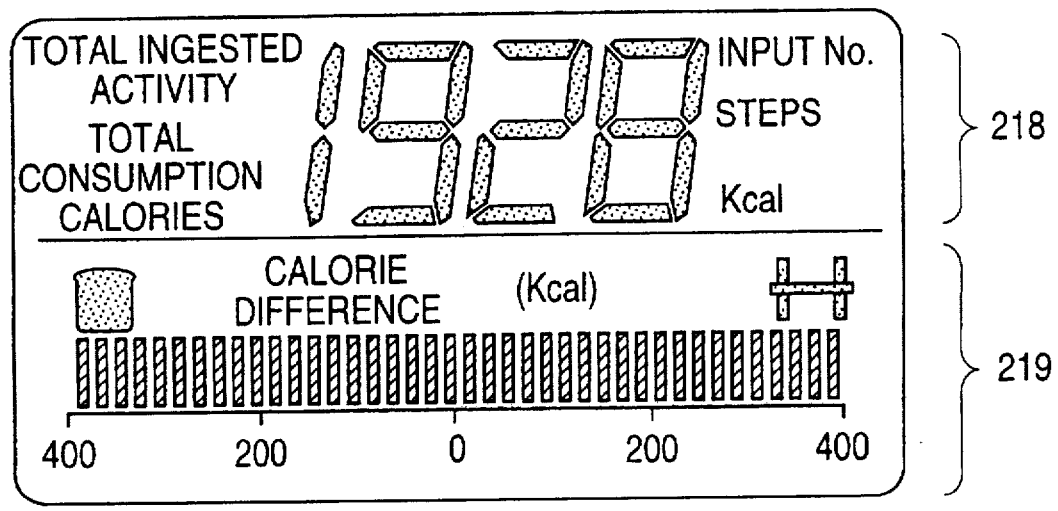
FIGS. 26A and FIG. 26B show a still another example of a display form in the third embodiment.
Figure 26B:
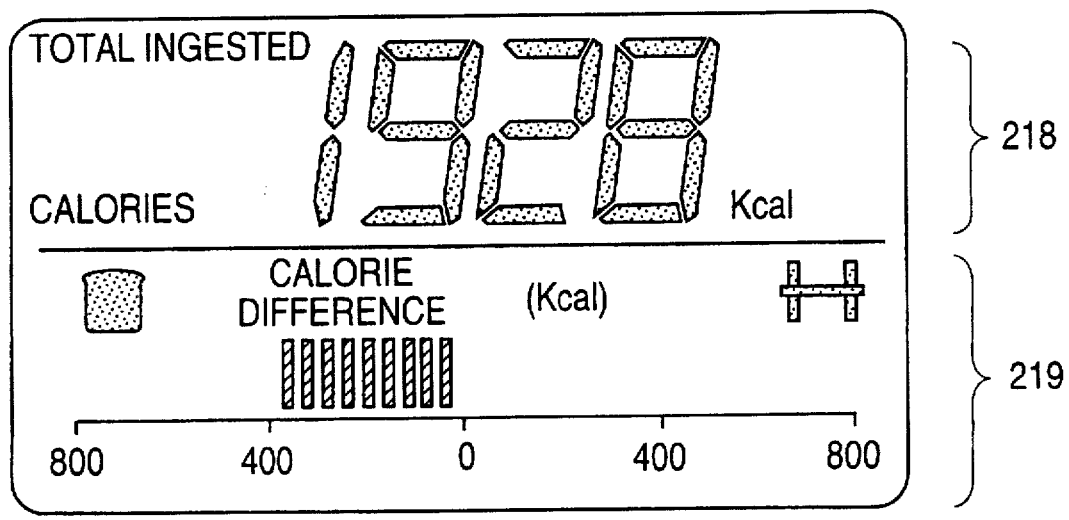

In a display form shown in FIGS. 26A and 26B, a difference (kcal) between ingested calories and consumed calories is displayed. In a case of FIG. 26A, the calorie difference is marked up to 400 kcal. In a case of FIG. 26B, the calorie difference is marked up to 800 kcal. An indication that is on the side of a slice of bread means that the ingested calories are larger than the consumed calories.

Figure 27:
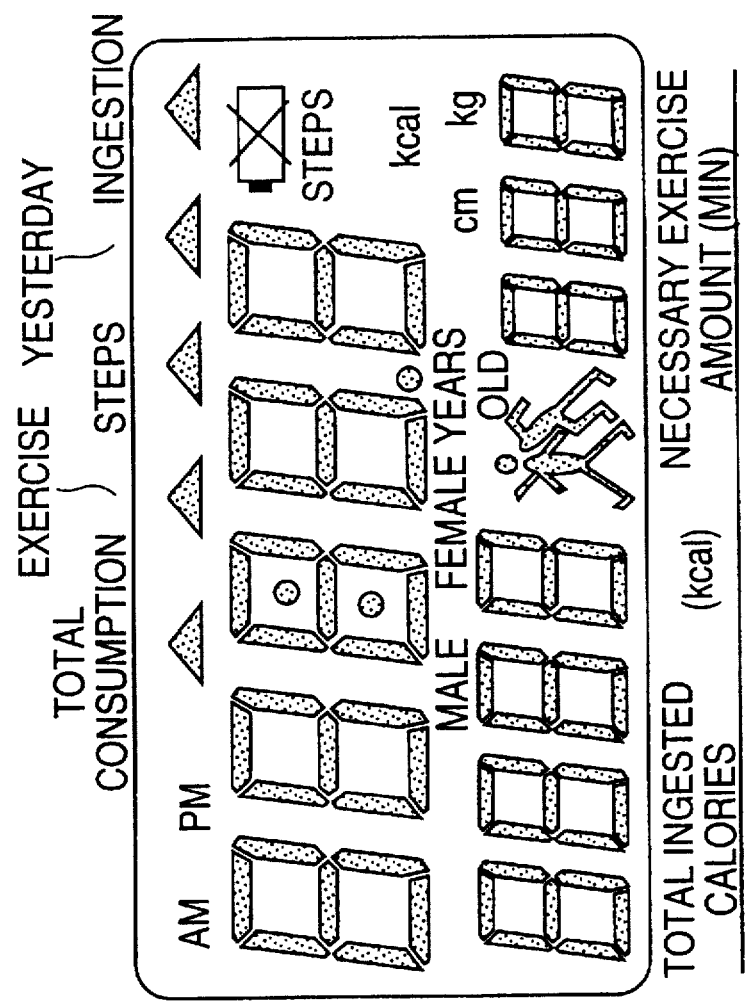
FIG. 27 and FIGS. 28A and 28B show another example of a display form in the third embodiment.
Figure 28A:
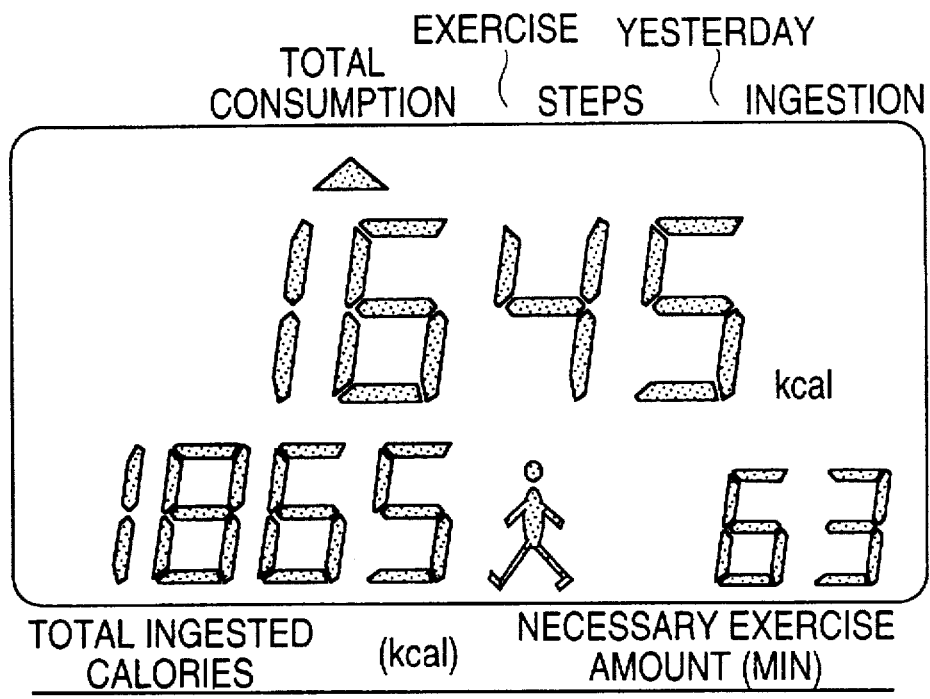
Figure 28B:
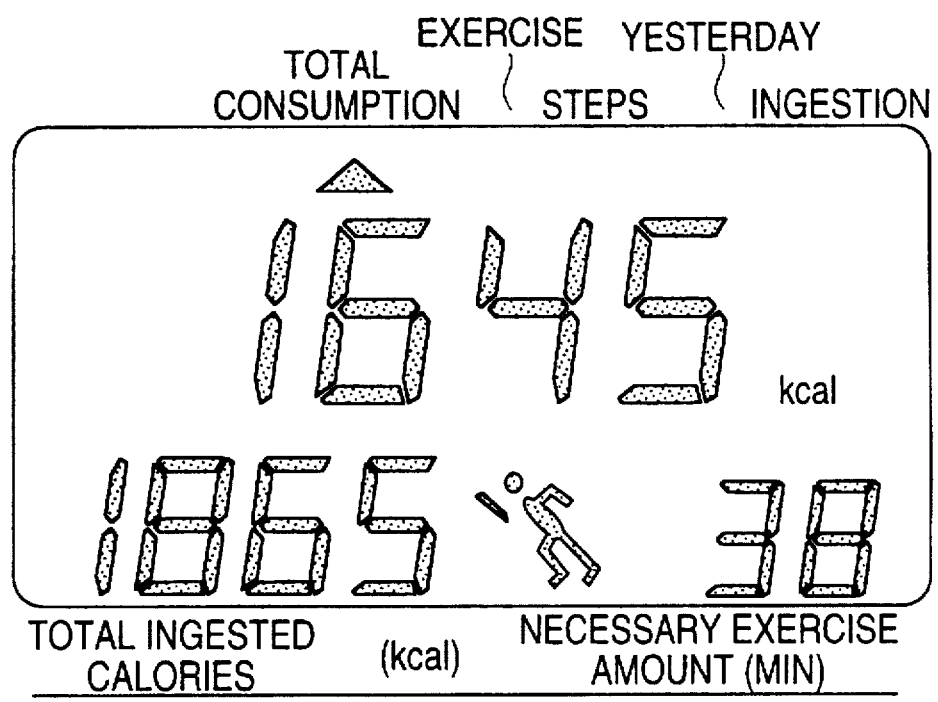

In a display form shown in FIG. 27, when ingested calories are larger than consumed calories, a type and a length of exercise that is necessary to consume excessive calories are displayed. FIGS. 28A and 28B show that ingested calories are 1,865 kcal and consumed calories are 1,645 kcal. Further, FIG. 28A indicates that walking of 63 minutes is needed to consume a difference 200 kcal. Similarly, FIG. 28B indicates that running of 38 minutes is needed. It goes without saying that switching between the display pictures of FIGS. 28A and 28B can be made by the select switch.

Next, with reference to a flowchart of FIGS. 29 and 30, a description will be made of an example of the entire operation of the above exercise amount measuring device. First, the power of the device is turned on in Step (hereinafter abbreviated as "ST") 201, and a gender, age, height and weight of a subject person are input in ST 202. In ST 203, a basal metabolism B is calculated, for instance, according to Equation (1). In ST 204, it is judged that the measurement start switch has been depressed. If the judgment result is negative, waiting is effected until the switch is depressed. Otherwise, the measurement is started. It goes without saying that the device has been mounted on the subject person before the measurement.

Upon the start of the measurement, an initial measurement is performed (ST 206), and data relating to a body movement of the subject person are acquired with the acceleration sensor 1 (ST 207). In ST 208, it is judged that acquired data have been accumulated for 10 seconds. If the judgment result is negative, it is then judged whether the keys for inputting ingested calories has been depressed (ST 209). If the judgment result in ST 209 is affirmative, ingested calories $A_f$ are input (ST 210) and the process returns to ST 207. If the judgment result in ST 209 is negative, the process returns to ST 207 skipping ST 210, to continue the data acquisition with the acceleration sensor 1. If the judgment result in ST 208 is affirmative, an exercise amount A (energy metabolism $E_{act}$) is calculated according to Equation (5) in ST 211 and displayed in ST 212.

After a difference ($A_f - A$) between the ingested calories $A_f$ and the exercise amount (consumed calories) A is calculated and displayed (ST 213), it is judged whether the ingested calories $A_f$ are larger than the consumed calories A (ST 214). If the judgment result is negative (i.e., $A_f \leq A$), ($A - A_f$)/γ is calculated and displayed (ST 215). The calculation of ($A_f - A$)/γ is to determine a food and its amount to be taken to get the calories now needed. Therefore, different values of the constant γ are set for respective foods. For example, γ is 160 kcal for a bowl of rice, 350 kcal for a bowl of udon (noodles), and 120 kcal for a slice of toast. Upon completion of ST 215, the process goes to ST 219.

If the judgment result in ST 214 is affirmative, ($A_f - A$)α$_1$, is calculated and displayed (ST 216), where α$_1$=3.5 kcal/min is a constant for walking. The calculation of ($A_f - A$)/α$_1$ is to determine how long walking should be performed to consume the excessive calories. In ST 217, it is judged whether the select switch has been depressed. If the judgment result is affirmative, ($A_f - A$)/α$_2$ is calculated and displayed (ST 218), where α$_2$=5 kcal/min is a constant for running. This calculation is to determine how long running should be performed to consume the excessive calories. In calculating ($A_f - A$)/α$_1$ and ($A_f - A$)/α$_2$, ($A_f - A - A'$) may be used in place of ($A_f - A$). The parameter A' is a quiet-state metabolism from the present time to time 0:00 and is calculated such that A'=1.2×B. By using ($A_f - A - A'$), the difference between the ingested calories and the consumed calories can be calculated more precisely. If the judgment result in ST 217 is negative, or if ST 218 has been executed, the process goes to ST 219.

In ST 219, it is judged whether 24 hours (one day) have passed from the measurement start. If the judgment result is negative, Steps 207–219 are repeated. If the judgment result is affirmative, the 24-hour data are updated and the consumed calories of the 24 hours and the corresponding comparison result between the ingested calories and the consumed calories are displayed in the above-described manner (ST 220). Then, the process returns to ST 206 to start data acquisition of the next 24 hours. It goes without saying that the 24-hour data are stored into the memory.

Figure 29:
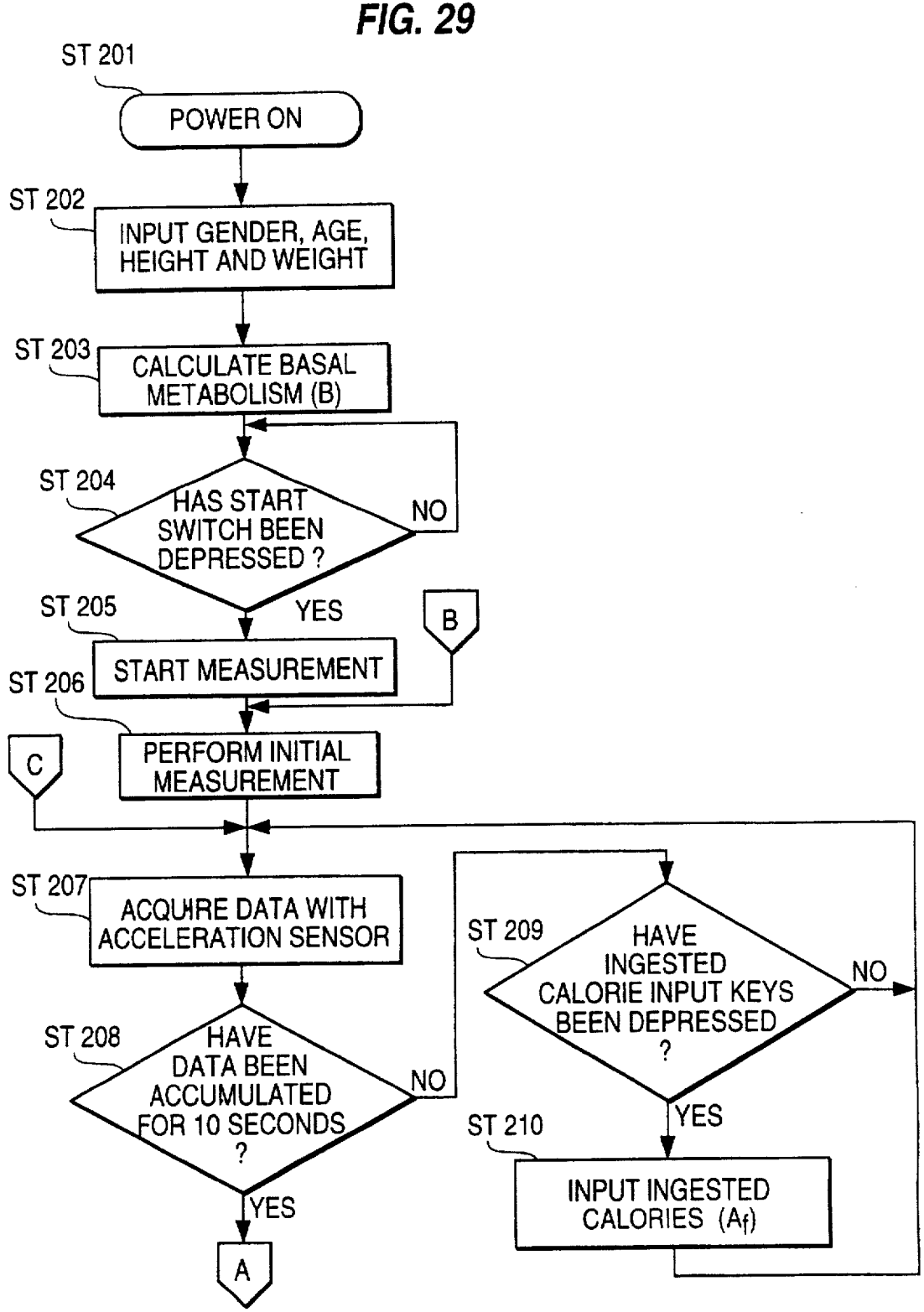
FIGS. 29 and 30 are a flowchart showing the entire operation of the exercise amount measuring device according to the third embodiment.
Figure 30:
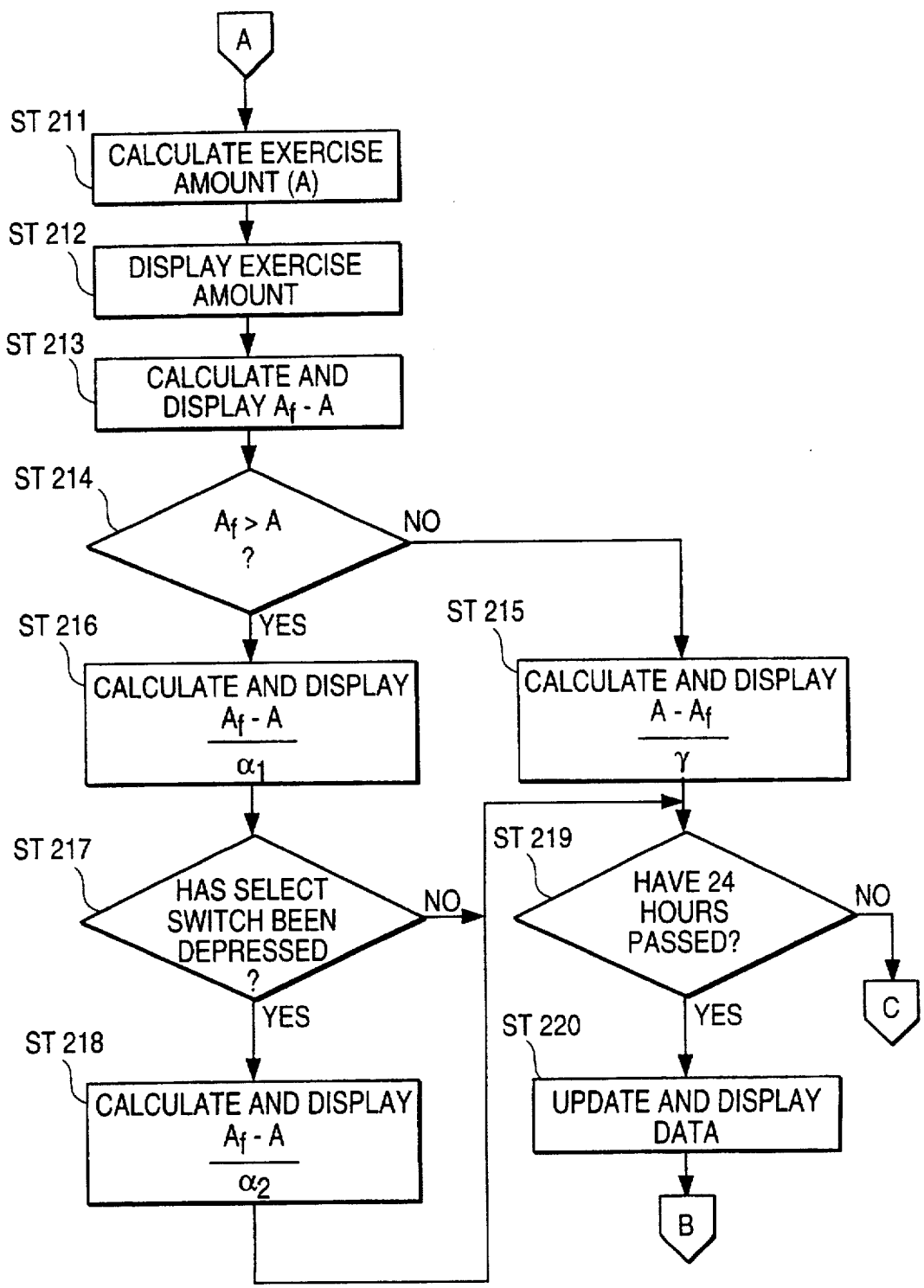
Figure 31:
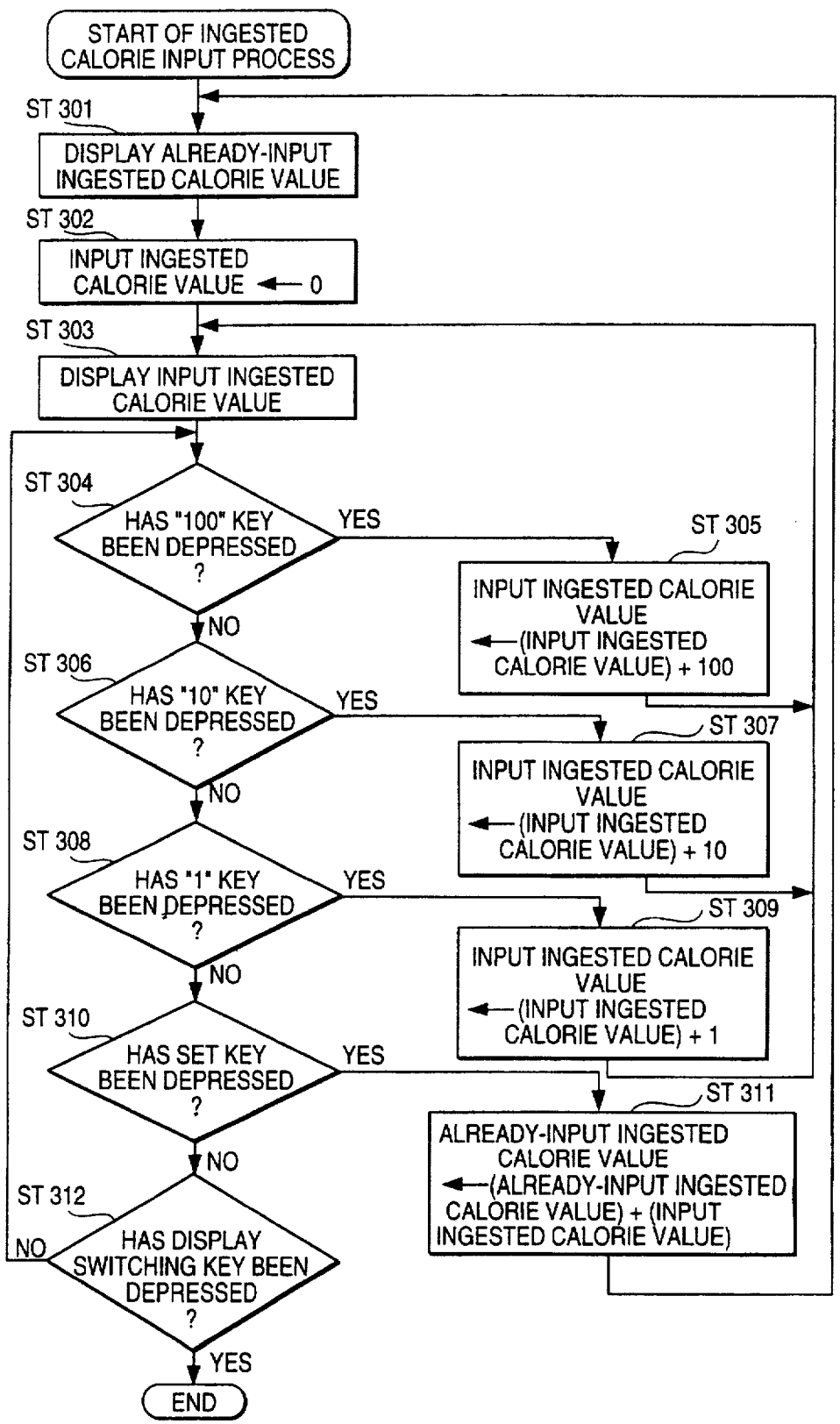
FIGS. 31 and 32 show specific examples of an ingested calorie input process in the process flow of FIGS. 29 and 30.

FIG. 31 shows a specific example of the ingested calorie input step (ST 210) of the process flow of FIGS. 29 and 30. This example is a case of inputting ingested calories directly. In this example, the ingested calorie input means consists of three keys, i.e., a "100" key, a "10" key, and a "1" key. Upon depression of those input keys, the already-input ingested calorie value (total ingested calorie value), which is the accumulated value of ingested calories input so far and is stored in the memory, is displayed (ST 301). At the same time, an input ingested calorie value to be used for inputting of this time is initialized to 0 (ST 302) and an input ingested calorie value "0" is displayed (ST 303).

In ST 304, it is judged whether the "100" key has been depressed. Upon every depression of the "100" key, a value obtained by adding 100 to the current input ingested calorie value is displayed as a new input ingested calorie value (Steps 305 and 303). Similarly, it is judged in ST 306 whether the "10" key has been depressed. Upon every depression of the "10" key, a value obtained by adding 10 to the current input ingested calorie value is displayed as a new input ingested calorie value (Steps 307 and 303). It is judged in ST 308 whether the "1" key has been depressed. Upon every depression of the "1" key, a value obtained by adding 1 to the current input ingested calorie value is displayed as a new input ingested calorie value (Steps 309 and 303). Then, in ST 310, it is judged whether the set key has been depressed. If the judgment result is affirmative, the input ingested calorie value just input above is added to the current already-input ingested calorie value; that is, the already-input ingested calorie value is updated (ST 311). Then, the process returns to ST 301, where the updated already-input ingested calorie value is displayed (see FIG. 23C and FIG. 25B). On the other hand, if the set key is not depressed (ST 310) and the display switching key is depressed (ST 312), the ingested calorie input process is finished. If the display switching key is not depressed (ST 312), the above loop of steps is repeated.

Figure 32:
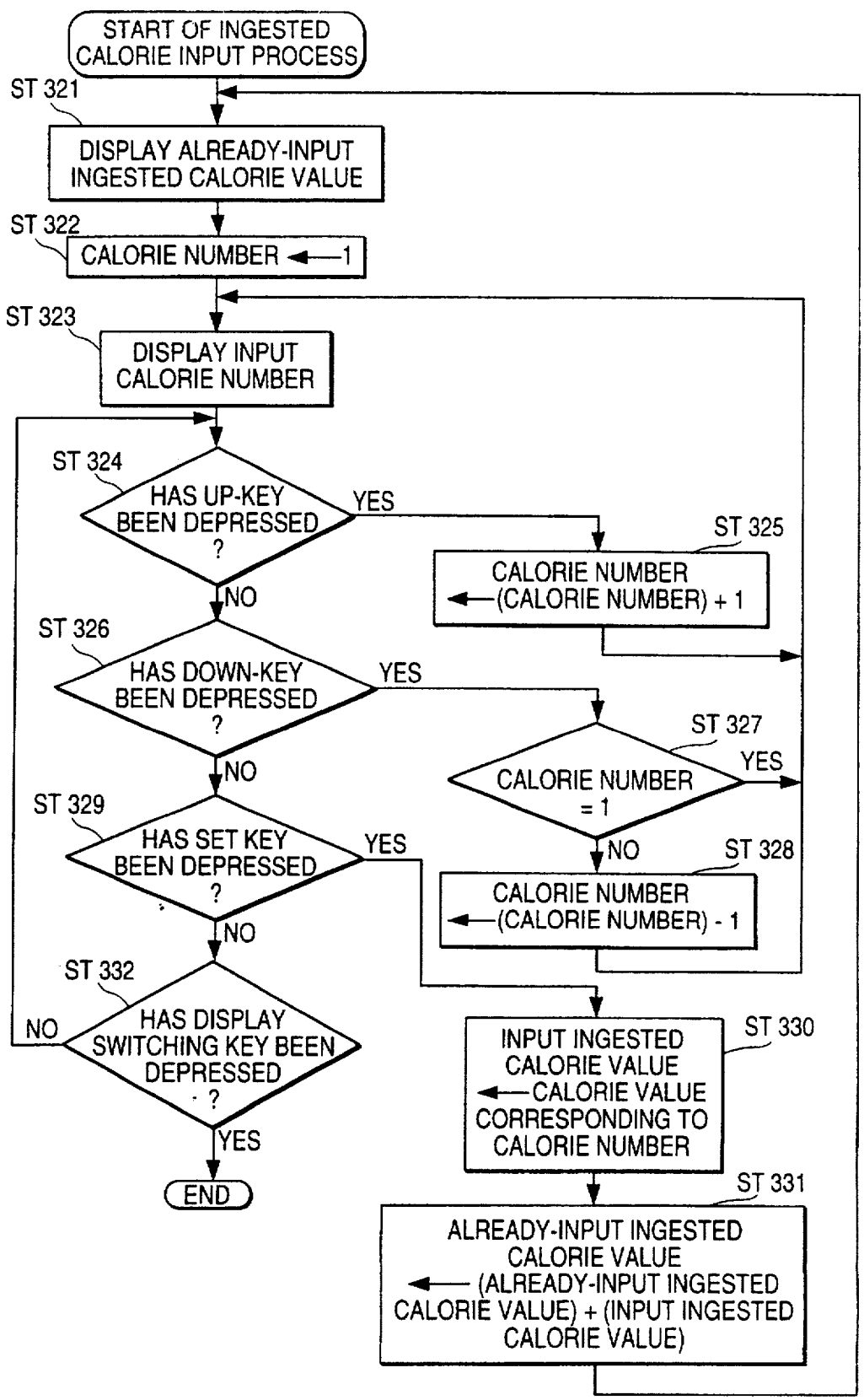
Figure 33:
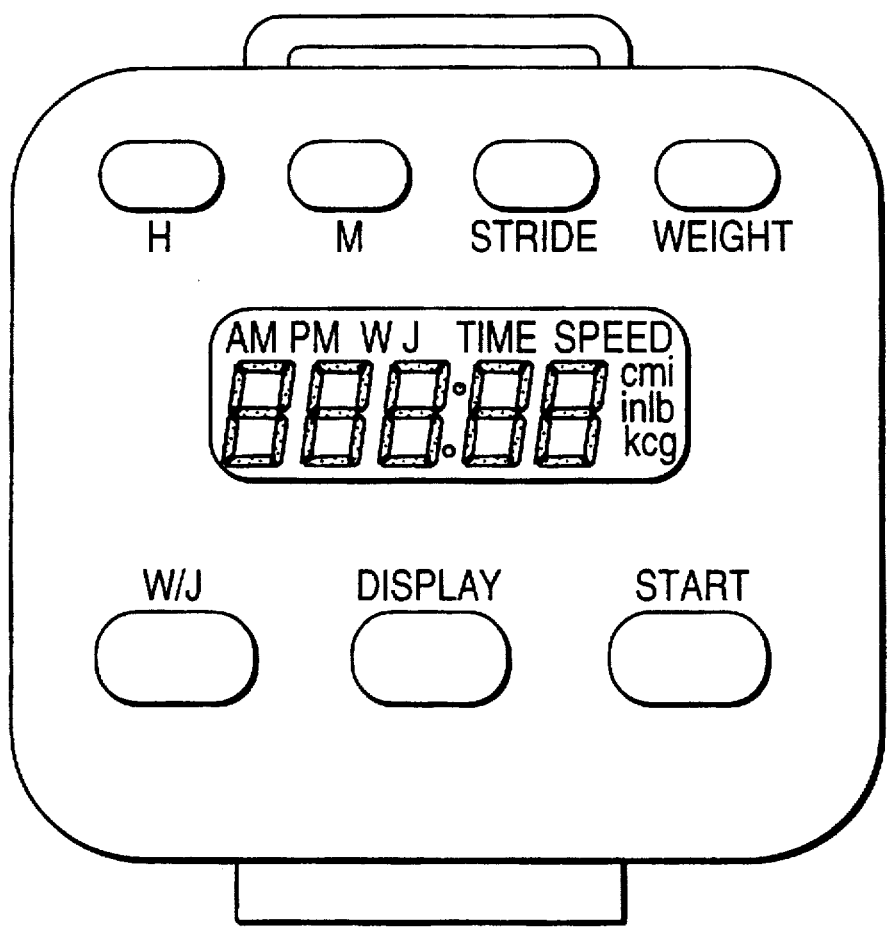
FIG. 33 shows an example of a display form employed in a conventional exercise amount measuring device.

FIG. 32 shows another specific example of the ingested calorie input process. This example is a case where the above-described menu sheet 230 is used for the input of ingested calories and a number listed on the menu sheet 230 is input through the up-key and the down-key. First, as in the above example, an already-input ingested calorie value is displayed (ST 321). At the same time, a calorie number is initialized to 1 (ST 322), and a calorie number "1" is displayed (ST 323). In ST 324, it is judged whether the up-key has been depressed (ST 324). Upon every depression of the up-key, a number obtained by adding 1 to the current calorie number is displayed as a new calorie number (Steps 325 and 323). In ST 326, it is judged whether the down-key has been depressed. Upon every depression of the down-key, a number obtained by subtracting 1 from the current calorie number is displayed as a new calorie number (Steps 328 and 323). If it is judged that the calorie number is equal to 1 in ST 327, the process goes to ST 323 skipping ST 328.

In ST 329, it is judged whether the set key has been depressed. If the judgment result is affirmative, a calorie value corresponding to the depressed calorie number (the former is stored in advance in the memory in association with the latter) is made an input ingested calorie value (ST 330). The input ingested calorie value thus set is added to the current already-input calorie value; that is, the already-input calorie value is updated (ST 331). Then, the process returns to ST 321, where the updated already-input ingested calorie number is displayed (see FIGS. 23A and 23B and FIG. 25A). This process is finished if the display switching key is depressed (ST 332). Otherwise, the above loop of steps is repeated.

Only one of the ingested calorie input processes of FIGS. 31 and 32 may be employed. Alternatively, both may be employed such that one of the two processes can be selected in accordance with a user's request.

What is claimed is:

1. An exercise amount measuring device comprising an acceleration sensor for detecting a body movement of a living body, means for calculating an exercise amount based on a detection signal of the acceleration sensor, a display section for displaying the calculated exercise amount, means for calculating a life activity index based on a measured exercise amount; and means for causing the display means to display the calculated life activity index, wherein the life activity index is calculated according to the following formula: 0.9×(total energy metabolism per day÷basal metabolism).

2. The exercise amount measuring device according to claim 1, wherein the life activity index is displayed in the form of one of ranks that have been preset by classifying the life activity index so that the ranks correspond to respective life activity intensities.

3. The exercise amount measuring device according to claim 2, wherein the difference is displayed in the form of an exercise time corresponding to the difference.

4. An exercise amount measuring device comprising an acceleration sensor for detecting a body movement of a living body, means for calculating an exercise amount based on a detection signal of the acceleration sensor, a display section for displaying the calculated exercise amount, means for classifying an action of the living body as one of a plurality of action types based on the detection signal of the acceleration sensor, calculating consumed energies of the respective action types, and calculating a total consumed energy from the calculated consumed energies; and means for causing the display section to display the calculated total consumed energy.

5. The exercise amount measuring device according to claim 4, wherein the action of the living body is classified by discriminating a pattern of an output waveform of the acceleration sensor.

6. The exercise amount measuring device according to claim 4, wherein the action types includes sleeping, sitting, standing, walking and running.

7. The exercise amount measuring device according to claim 4, further comprising means for causing the display section to display a ratio among time lengths of the respective action types.

8. The exercise amount measuring device according to claim 4, further comprising means for causing the display section to display a pattern of occurrence of the action types in a time order at predetermined time intervals.

9. The exercise amount measuring device according to claim 5, wherein an average of amplitudes of acceleration of one-step sections of the acceleration waveform is calculated, and the action is judged to be walking if the average is smaller than or equal to a prescribed amplitude, and to be running if the average is larger than the prescribed amplitude, wherein the action is judged to be standing if downward acceleration appears first and upward acceleration appears next in the acceleration waveform, and to be sitting if upward acceleration appears first and downward acceleration appears next in the acceleration waveform, and wherein the action is judged to be sleeping if there occurs no variation in the acceleration waveform in a prescribed period.

10. An exercise amount measuring device comprising an acceleration sensor for detecting a body movement of a living body, means for calculating an exercise amount based on a detection signal of the acceleration sensor, a display section for displaying the calculated exercise amount, means for classifying an action of the living body as one of a plurality of action types, calculating consumed energies of the respective action types, and calculating a total consumed energy from the calculated consumed energies; and means for causing the display section to display the calculated total consumed energy, wherein the consumed energy of each action is calculated according to the following formula:
{(relative metabolic rate of the action)+1.2}×(time length of the action)×(basal metabolism).

* * * * *